US009040590B2

(12) United States Patent
Yacoby-Zeevi et al.

(10) Patent No.: US 9,040,590 B2
(45) Date of Patent: *May 26, 2015

(54) CONTINUOUS ADMINISTRATION OF DOPA DECARBOXYLASE INHIBITORS AND COMPOSITIONS FOR SAME

(71) Applicant: Neuroderm, Ltd., Ness-Ziona (IL)

(72) Inventors: Oron Yacoby-Zeevi, Moshav Bitsaron (IL); Mara Nemas, Gedera (IL)

(73) Assignee: NeuroDerm, Ltd., Rehovot (IL)

( * ) Notice: Subject to any disclaimer, the term of this patent is extended or adjusted under 35 U.S.C. 154(b) by 0 days.

This patent is subject to a terminal disclaimer.

(21) Appl. No.: 14/276,235

(22) Filed: May 13, 2014

(65) Prior Publication Data

US 2014/0249231 A1    Sep. 4, 2014

Related U.S. Application Data

(63) Continuation of application No. 12/961,534, filed on Dec. 7, 2010, which is a continuation of application No. 12/836,130, filed on Jul. 14, 2010, now Pat. No. 7,863,336, which is a continuation of application No. 12/781,357, filed on May 17, 2010, now Pat. No. 8,193,243.

(60) Provisional application No. 61/179,511, filed on May 19, 2009.

(51) Int. Cl.
| | |
|---|---|
| *A61K 31/198* | (2006.01) |
| *A61K 47/18* | (2006.01) |
| *A61K 9/00* | (2006.01) |
| *A61K 31/12* | (2006.01) |
| *A61K 31/277* | (2006.01) |
| *A61K 47/22* | (2006.01) |

(52) U.S. Cl.
CPC ............. *A61K 47/183* (2013.01); *A61K 9/0019* (2013.01); *A61K 31/12* (2013.01); *A61K 31/198* (2013.01); *A61K 31/277* (2013.01); *A61K 47/22* (2013.01)

(58) Field of Classification Search
CPC ........................... A61K 31/198; A61K 47/183
See application file for complete search history.

(56) References Cited

U.S. PATENT DOCUMENTS

| | | | |
|---|---|---|---|
| 3,936,495 | A | 2/1976 | Sullivan, Jr. |
| 4,241,082 | A | 12/1980 | Baba et al. |
| 4,409,233 | A | 10/1983 | Tsukada et al. |
| 4,642,316 | A | 2/1987 | Fawzi et al. |
| 4,684,666 | A | 8/1987 | Haas |
| 4,826,875 | A | 5/1989 | Chiesi |
| 4,963,568 | A | 10/1990 | Schoenleber et al. |
| 5,350,769 | A | 9/1994 | Kasai et al. |
| 5,861,423 | A | 1/1999 | Caldwell et al. |
| 5,877,176 | A | 3/1999 | Gross |
| 6,153,615 | A | 11/2000 | Gross |
| 6,166,083 | A | 12/2000 | Barrett et al. |
| 6,245,917 | B1 | 6/2001 | Bosch et al. |
| 6,274,168 | B1 | 8/2001 | Addicks et al. |
| 6,348,965 | B1 | 2/2002 | Palladino et al. |
| 6,500,867 | B1 | 12/2002 | Virkki et al. |
| 6,620,432 | B2 | 9/2003 | Addicks et al. |
| 6,716,452 | B1 | 4/2004 | Piccariello et al. |
| 6,878,529 | B2 | 4/2005 | Harrow et al. |
| 6,974,591 | B2 | 12/2005 | Kendrup et al. |
| 7,201,923 | B1 | 4/2007 | van Lengerich |
| 7,223,776 | B2 | 5/2007 | Surivet et al. |
| 7,309,719 | B1 | 12/2007 | Aomatsu |
| 7,479,498 | B2 | 1/2009 | Keller |
| 7,560,100 | B2 | 7/2009 | Pinchasi et al. |
| 7,589,233 | B2 | 9/2009 | Chandran |
| 7,709,494 | B2 | 5/2010 | Defossa et al. |
| 7,863,336 | B2 | 1/2011 | Yacoby-Zeevi et al. |
| 8,058,243 | B2 | 11/2011 | Tyers et al. |
| 8,173,840 | B2 | 5/2012 | Chandran |
| 8,193,243 | B2 | 6/2012 | Yacoby-Zeevi et al. |
| 8,263,125 | B2 | 9/2012 | Vaya et al. |
| 2002/0028799 | A1 | 3/2002 | Naylor et al. |
| 2002/0099013 | A1 | 7/2002 | Piccariello et al. |
| 2003/0119714 | A1 | 6/2003 | Naylor et al. |
| 2005/0053669 | A1 | 3/2005 | Friedl et al. |
| 2005/0163850 | A1 | 7/2005 | Wong et al. |
| 2005/0233945 | A1 | 10/2005 | Brown et al. |
| 2006/0041014 | A1 | 2/2006 | Naylor et al. |

(Continued)

FOREIGN PATENT DOCUMENTS

| | | |
|---|---|---|
| CN | 101669925 A | 3/2010 |
| DE | 2838232 A1 | 3/1979 |

(Continued)

OTHER PUBLICATIONS

Pardo et al. Mov. Disorders, 1993, Issue 3, Abstract.*
"Duodopa Intestinal Gel," retrieved from https://www.medicines.org.uk/emc/medicine/20786/SPC/Duodopa+intestinal+gel/#composition (2013), 7 pages.
"Pharmacokinetics of Levodopa/Carbidopa Infusion With and Without Oral Catechol-O-Methyl Transferase (COMT) Inhibitors (DuoCOMT)," retrieved from URL://http://clinicaltrials.gov/ct2/show/NCT00906828 (2010), 3 pages.
Gordon, M., et al., (2007) "Intravenous Levodopa Administration in Humans Based on a Two-Compartment Kinetic Model," *J. Neuroscience Methods*, 159: 300-307.

(Continued)

*Primary Examiner* — Samira Jean-Louis
(74) *Attorney, Agent, or Firm* — Goodwin Procter LLP

(57) ABSTRACT

Disclosed herein are compositions that include for example the arginine salt of carbidopa, and methods for treating neurological or movement diseases or disorders such as restless leg syndrome, Parkinson's disease, secondary parkinsonism, Huntington's disease, Parkinson's like syndrome, PSP, MSA, ALS, Shy-Drager syndrome and conditions resulting from brain injury including carbon monoxide or manganese intoxication, using substantially continuous administration of carbidopa or salt thereof together with administration of levodopa.

17 Claims, 18 Drawing Sheets

(56) References Cited

U.S. PATENT DOCUMENTS

| | | |
|---|---|---|
| 2006/0159751 A1 | 7/2006 | Gogia et al. |
| 2006/0241183 A1 | 10/2006 | Karoum |
| 2008/0051459 A1 | 2/2008 | Nyholm et al. |
| 2008/0255235 A1 | 10/2008 | Segrell |
| 2010/0298428 A1 | 11/2010 | Yacoby-Zeevi et al. |
| 2011/0269833 A1 | 11/2011 | Yacoby-Zeevi et al. |
| 2012/0115823 A1 | 5/2012 | Price et al. |
| 2013/0116215 A1 | 5/2013 | Coma et al. |
| 2013/0123485 A1 | 5/2013 | Park et al. |
| 2013/0253056 A1 | 9/2013 | Nemas et al. |
| 2013/0338143 A1 | 12/2013 | Yacoby-Zeevi et al. |
| 2014/0051755 A1 | 2/2014 | Yacoby-Zeevi et al. |

FOREIGN PATENT DOCUMENTS

| | | |
|---|---|---|
| EP | 1077692 A1 | 2/2001 |
| IN | 244675 B | 12/2010 |
| IN | 251149 B | 2/2012 |
| JP | 54050700 A | 4/1979 |
| WO | WO-00/54773 A1 | 9/2000 |
| WO | WO-01/01984 A1 | 1/2001 |
| WO | WO-2005/099678 A1 | 10/2005 |
| WO | WO-2006/006929 A1 | 1/2006 |
| WO | WO-2007/138086 A1 | 12/2007 |
| WO | WO-2010/134074 A1 | 11/2010 |
| WO | WO-2012/006959 A1 | 1/2012 |
| WO | WO-2012/066538 A1 | 5/2012 |

OTHER PUBLICATIONS

Hirano, et al., (2008) "Arginine Increases the Solubility of Coumarin: Comparison with Salting-in and Salting-out Additives," *J. Biochem*, 144 (3): 363-369.

International Search Report for PCT/IL2010/000400, mailed Jul. 29, 2010, 4 pages.

International Search Report for PCT/IL2011/000881, mailed Apr. 3, 2012, 4 pages.

International Search Report for PCT/IL2014/050261, mailed May 30, 2014, 5 pages.

Mehlisch, et al., (2002) "A Controlled Comparative Study of Ibuprofen Arginate Versus Conventional Ibuprofen in the Treatment of Postoperative Dental Pain," *J. Clin. Pharmacol.*, 42: 904-911.

Movement Disorders "Levodopa" (2002) 17: S23-S37.

Nahata, et al., (2000) "Development of Two Stable Oral Suspensions of Levodopa-Carbidopa for Children with Amblyopia," *J. Pediatric Ophthal. & Strab.*, 37:333-337.

Nord, M. (2010) The Effect of Peripheral Enzyme Inhibitors on Levodopa Concentrations in Blood and CSF, *Movement Disorders*, 25(3): 363-367.

Nutt, et al., (1997) "Motor Fluctuations During Continuous Levodopa Infusions in Patients with Parkinson's Disease," *Movement Disorders*, 12(3):285-292.

Nyholm, D. (2006) "Enteral Levodopa/Carbidopa Gel Infusion for the Treatment of Motor Fluctuations and Dyskinesias in Advanced Parkinson's Disease," *Expert Review of Neurotherapeutics*, 6(10): 1403-1411.

Nyholm, D. (2012) "Levodopa Infusion Combined with Entacapone or Tolcapone in Parkinson Disease: a Pilot Trial," *European Journal of Neurology*, 19: 820-826.

Olanow, C.W. (2008) "Levopoda/Dopamine Replacement Strategies in Parkinson's Disease—Future Directions," *Movement Disorders*, 23:S613-S622.

Redenti, et al. (2001) "Cyclodextrin Complexes of Salts of Acidic Drugs. Thermodynamic Properties, Structural Features, and Pharmaceutical Applications," *Journal of Pharmaceutical Sciences*, 90(8): 979-986.

Tsumoto, K., et al., (2004) "Role of Arginine in Protein Refolding, Solubilization, and Purification," *Biotechnol. Prog.*, 20:1301-1308.

Written Opinion of the International Search Authority for PCT/IL2010/000400 mailed Aug. 29, 2010, 8 pages.

Written Opinion of the International Search Authority for PCT/IL2011/000881 mailed May 15, 2013, 6 pages.

Written Opinion of the International Search Authority for PCT/IL2014/050261 mailed May 30, 2014, 6 pages.

Yacoby-Zeevi, O., et al. (2010) "Markedly Enhanced Levodopa Pharmacokinetics from Continuous Subcutaneous Carbidopa Administration," *European Journal of Neurology*, 17 (Suppl. 3): 52.

Martinez et al., "Hypothesis: Can N-Acetylcysteine Be Beneficial in Parkinson's Disease?", Life Sciences, 64(15):1253-1257 (1999).

\* cited by examiner

Fig. 4A1
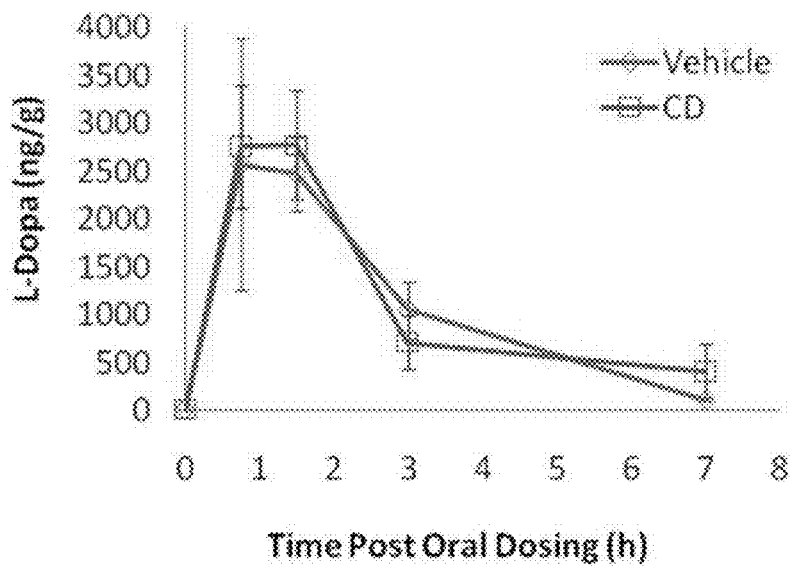
Fig. 4A2
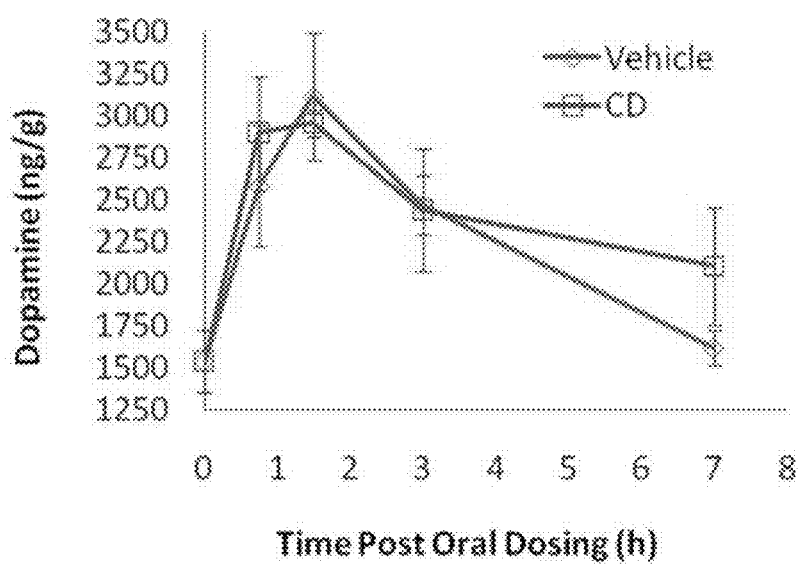

Fig. 4B1
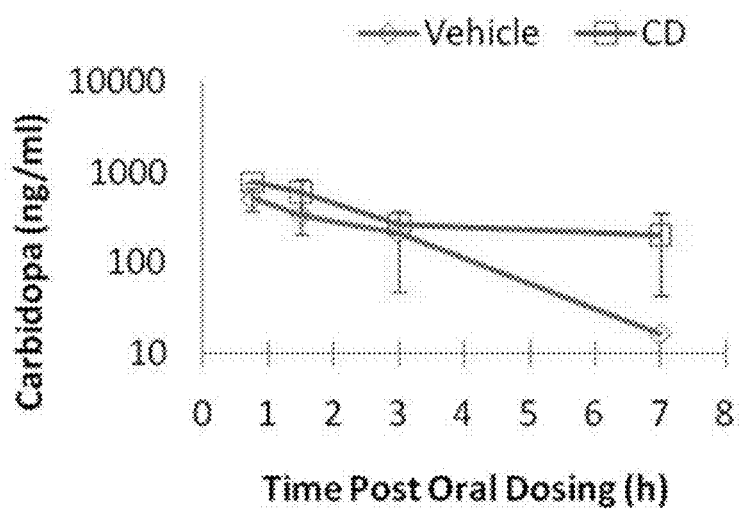
Fig. 4B2
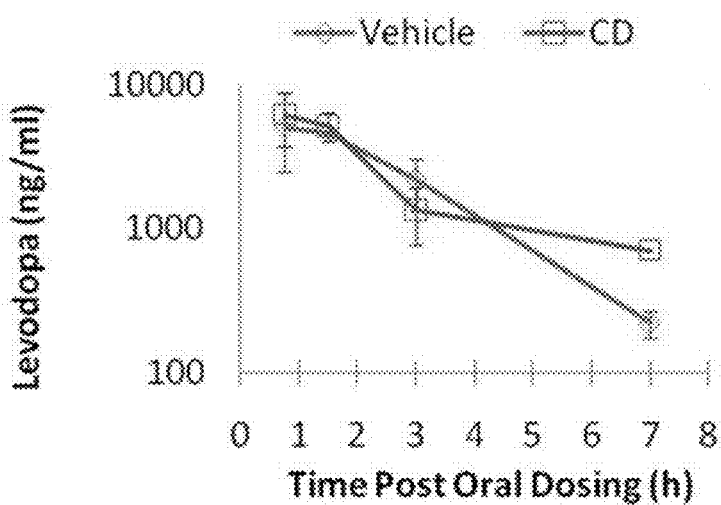

Oral dosing of LD/CD

CONTINUOUS ADMINISTRATION OF DOPA DECARBOXYLASE INHIBITORS AND COMPOSITIONS FOR SAME

RELATED APPLICATION

This application is a continuation of U.S. Ser. No. 12/961,534, filed Dec. 7, 2010, which is a continuation of U.S. Ser. No. 12/836,130, filed Jul. 14, 2010, now U.S. Pat. No. 7,863,336, issued Jan. 4, 2011, which is a continuation of U.S. Ser. No. 12/781,357, filed May 17, 2010, now U.S. Pat. No. 8,193,243, issued Jun. 5, 2012, which claims priority to U.S. Ser. No. 61/179,511, filed May 19, 2009, all of which are hereby incorporated by reference in its entirety.

BACKGROUND

Parkinson's disease is a degenerative condition characterized by reduced concentration of the neurotransmitter dopamine in the brain. Levodopa (L-dopa or L-3,4-dihydroxyphenylalanine) is an immediate metabolic precursor of dopamine that, unlike dopamine, is able to cross the blood-brain barrier, and is most commonly used for restoring the dopamine concentration in the brain. For the past 40 years, levodopa has remained the most effective therapy for the treatment of Parkinson's disease.

However, levodopa has a short half life in plasma that, even under best common current standard of care, results in pulsatile dopaminergic stimulation. Long-term therapy is therefore complicated by motor fluctuations and dyskinesia that can represent a source of significant disability for some patients. A therapeutic strategy that could ultimately deliver levodopa/dopamine to the brain in a more continuous and physiologic manner would provide the benefits of standard levodopa with reduced motor complications and is much needed by patients suffering from Parkinson's disease and other neurological or movement disorders (Olanow CW; Mov. Dis. 2008, 23(Suppl. 3):S613-S622). Sustained-release oral levodopa formulations have been developed, but, at best, such preparations have been found to be no more efficacious than standard tablets. Continuous administration of levodopa by intraduodenal administration or infusion has also been attempted by using ambulatory pumps or patches. Such treatments, especially intraduodenal, are extremely invasive and inconvenient. Further, such treatments may be associated with dopaminergic adverse events; continuous administration of levodopa or dopa agonists is still associated with off periods that are self-limiting despite continued delivery of the drug. Nutt JG; Mov. Dis. 2008, 23(Suppl. 3):5580-4.

The metabolic transformation of levodopa to dopamine is catalyzed by the aromatic L-amino acid decarboxylase enzyme, a ubiquitous enzyme with particularly high concentrations in the intestinal mucosa, liver, brain and brain capillaries. Due to the possibility of extracerebral metabolism of levodopa, it is necessary to administer large doses of levodopa leading to high extracerebral concentrations of dopamine that cause nausea in some patients. Therefore, levodopa is usually administered concurrently with oral administration of a dopa decarboxylase inhibitor, such as carbidopa or benserazide, which reduces by 60-80% the levodopa dose required for a clinical response, and thus prevents certain of its side effects by inhibiting the conversion of levodopa to dopamine outside the brain. Exactly how this dose reduction is accomplished is uncertain. Various formulations comprising levodopa alone or together with inhibitors of enzymes associated with the metabolic degradation of levodopa are well known, for example, decarboxylase inhibitors such as carbidopa and benserazide, catechol-O-methyl transferase (COMT) inhibitors such as entacapone and tolcapone, and monoamone oxidase (MAO)-A or MAO-B inhibitors such as moclobemide, rasagiline or selegiline or safinamide. Currently available oral drugs include SINEMET® and SINEMET®CR sustained-release tablets that include carbidopa or levodopa; STA-LEVO® tablets containing carbidopa, entacapone and levodopa; and MADOPAR® tablets containing levodopa and benserazide. There is an on-going and urgent need for methods and compositions that can effect continuous stimulation of L-dopa to more effectively treat movement disorders such as Parkinson's disease.

Carbidopa [(−)-L-α-hydrazino-α-methyl-β-(3,4-dihydroxybenzene) propanoic acid monohydrate], a white, crystalline compound, only slightly soluble in water, is a dopa decarboxylase inhibitor commonly administered with levodopa. Only 40-70% of an oral dose of carbidopa is absorbed in man, monkey and dog. Although carbidopa has been orally administered with levodopa for over 30 years, no stable liquid formulation having e.g., an effective concentration in a volume suitable for use for subcutaneous or transdermal delivery has ever been achieved. There is an urgent, long standing need for such carpidopa formulations that can be administered more easily to patients, especially as compared to current invasive modes such as duodenal administration.

SUMMARY

This disclosure relates at least in part to the discovery that an arginine salt of carbidopa can form a stable, liquid formulation, suitable for e.g., continuous subcutaneous, transdermal, intradermal, intravenous and/or intraduodenal administration, at a physiologically acceptable pH. Such disclosed compositions are capable of substantially continuously administering carbidopa to a patient in need thereof. For example, disclosed herein are compositions that relate to the disclosed discovery that substantially continuously administering a dopa decarboxylase inhibitor such as carbidopa, together with discrete (e.g. oral) co-administration of levodopa, may stimulate L-dopa substantially continuously and thus e.g., extend the effectiveness of a levodopa oral dosing regimen and/or reduce the daily dosage of levodopa, while effectively treating a movement and/or neurological disorder such as Parkinson's disease.

In an embodiment, this disclosure provides for carbidopa and/or levodopa salts with a basic amino acid such as arginine. For example, the disclosure provides for an arginine salt of levodopa or carbidopa that is suitable for e.g., continuous subcutaneous, trandermal, intradermal, intravenous, oral, or intraduodenal administration.

Also contemplated herein are pharmaceutically acceptable liquid (e.g., liquid at room temperature) or gel formulations or compositions that include an arginine salt of carbidopa, e.g., include carbidopa and arginine, that may be suitable for substantially continuous administration to a patient e.g. with or without use of, for example, a transdermal patch or subcutaneous pump (e.g. an insulin-like pump). Such contemplated liquid compositions may include at least 1%, at least 4%, at least 6% or more by weight carbidopa, (e.g. about 2% to about 6% by weight carbidopa) and therefore may facilitate administration of smaller amounts of a pharmacologically acceptable formulation to achieve efficacy as compared to a carbidopa formulation that is only capable of having less than 1% by weight carbidopa. In another embodiment, contemplated herein is a liquid or gel composition that includes a molar ratio of about 1.0:0.5 to about 1:to about 2.5, e.g., 1:1.0-1.2 molar ratio of carbidopa:basic amino acid, e.g. carbidopa: arginine. A liquid composition that includes carbidopa and a basic amino acid, as contemplated herein, may have a physiologically acceptable pH, e.g. a pH of about 6.5 to 9.5, e.g., about 7 to about 9, or about 8 to about 9, at 25° C.

In yet another embodiment, contemplated herein is a pharmaceutically acceptable liquid or gel composition that includes a molar ratio of about 1.0:0.5 to about 1:2, e.g., about 1:1.8 molar ratio of levodopa:arginine. For example, provided herein is a liquid composition that may include at least about 4% by weight, or at least 5%, at least about 6% (e.g. about 3% to about 7%) or more by weight levodopa. A liquid composition having levodopa and a basic amino acid, as contemplated herein, may have a pH of about 8 to 10, e.g., about 8.5 to about 9.5, at 25° C.

Exemplary liquid compositions contemplated herein may be liquid solutions, e.g. may be a substantially homogenous mixture that includes carbidopa and arginine, and may include water, or alternatively may be substantially non-aqueous. In other embodiments, contemplated compositions may also include other active agents such as entacapone and/or tolcapone and/or may include one or more pharmaceutically acceptable excipients such as N-methylpyrrolidone (NMP), polyvinylpyrrolidone (PVP), propylene glycol, antioxidants, or combinations thereof.

In some embodiments, disclosed compositions, e.g. liquid compositions, may be substantially stable at 25° C. for at least about 48 hours or more.

In one aspect, provided herein is a kit comprising a first formulation suitable for continuous administration to a patient comprising an arginine:carbidopa salt and a second formulation suitable for e.g. oral administration comprising levodopa or an arginine salt of levodopa and optionally instructions for use.

Also provided herein, in one embodiment, is a method for treatment of a disease or disorder characterized by reduced levels of dopamine in a patient's brain, (e.g. Parkinson's disease), comprising substantially continuously administering to a patient in need thereof a therapeutically effective amount of a decarboxylase inhibitor, a salt or an ester thereof, and administering a therapeutically effective amount of levodopa or pharmaceutically acceptable salt thereof (e.g., arginine levodopa), or composition comprising levodopa (for example, administering a composition e.g. a tablet, having levodopa as its sole active agent, or a composition that includes levodopa and one or more other active agents such as carbidopa, benserazide, entacapone, tolcapone, selegiline and/or rasagiline. Contemplated methods of treatment included those directed to diseases or disorders including restless leg syndrome, Parkinson's disease, secondary parkinsonism, Huntington's disease, Parkinson's like syndrome, progressive supranuclear palsy (PSP), multiple system atrophy (MSA), amyotrophic lateral sclerosis (ALS), Shy-Drager syndrome and conditions resulting from brain injury including carbon monoxide or manganese intoxication. In an embodiment, continuous administering may include transdermal, intradermal, subcutaneous, intravenous, or intraduodenal administration, e.g. may include the use of an infusion pump.

In one embodiment, a method of treating or ameliorating a neurological or movement disorder in a patient in need thereof is provided comprising: administering a therapeutically effective amount of a composition comprising a carbidopa basic amino acid salt (e.g., carbidopa arginine) and administering a therapeutically effective amount of a composition comprising levodopa. For example, a composition comprising carbidopa and arginine may be administered substantially continuously and/or the composition comprising levodopa may be administered at discrete intervals (for example by oral administration one, two, three or more times a day), during the substantially continuous administration of composition comprising a carbidopa arginine salt.

Also provided herein is a method of substantially continuously inhibiting decarboxylase activity and/or a method of increasing the half-life of levodopa in a patient receiving levodopa, comprising administering (e.g. substantially continuously) to the patient a liquid or gel composition comprising a carbidopa salt such as carbidopa arginine. For example, the disclosed methods may result in a half-life of levodopa in the plasma of a patient that is at least 1.5, or at least two times, longer after continuous administration of carbidopa as compared to the half life of levodopa in a patient's serum after administering levodopa with discrete, oral administration of carbidopa.

BRIEF DESCRIPTION OF THE FIGURES

FIGS. 4A1-4A2 and 4B1-4B2 show brain levels of dopamine and L-Dopa (4A1 and 4A2), and plasma levels of L-dopa and carbidopa (4B1 and 4B2, respectively) determined in CD-1 mice following oral administration of levodopa/carbidopa with or without continuous subcutaneous administration of carbidopa.

DETAILED DESCRIPTION OF THE INVENTION

Figure 1A:
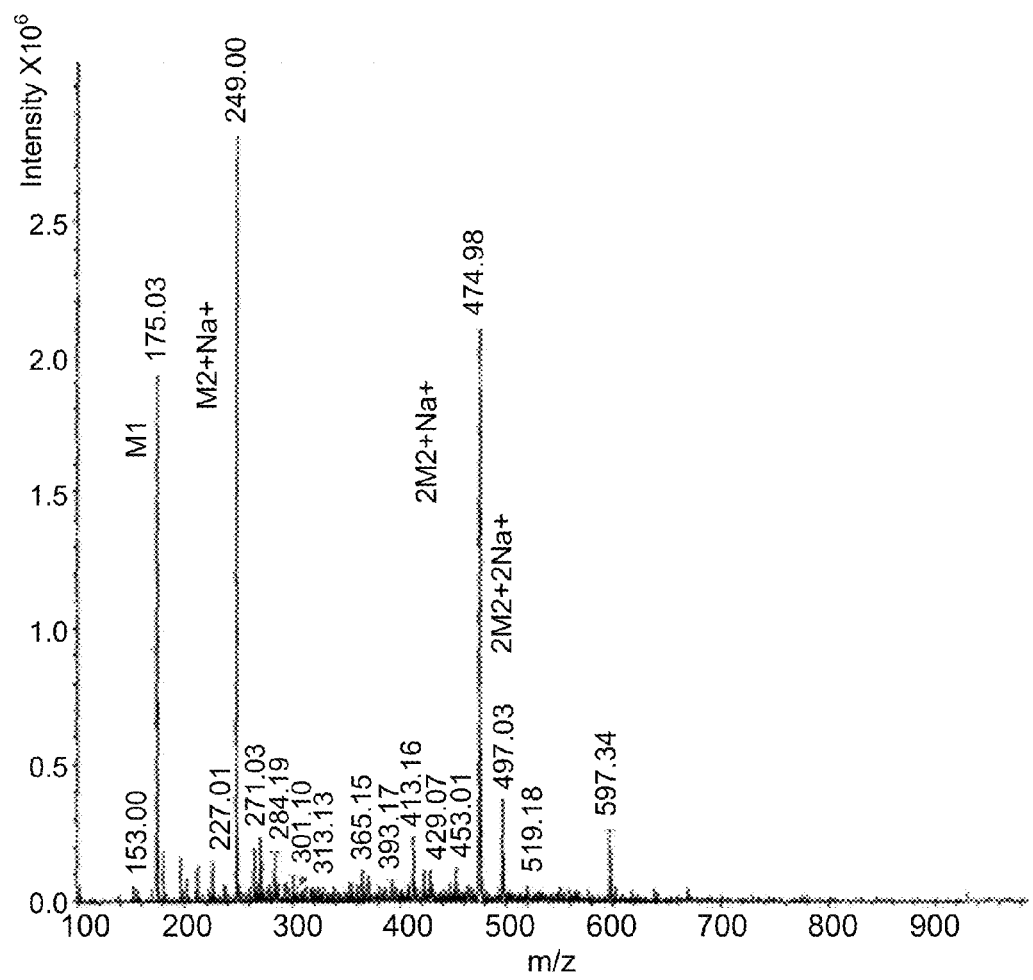
FIGS. 1A-1C depict the mass spectra of carbidopa arginine salt.

Disclosed herein is a liquid composition having a physiologically acceptable pH that includes an arginine salt of carbidopa (e.g., arginine and carbidopa) that is stable at room temperature, which can facilitate continuous delivery of an effective amount carbidopa to a patient in a minimally invasive fashion (e.g. a disclosed liquid formulation comprises a significantly high concentration of carbidopa so that administration of large amounts of liquid are not required) Such formulations may facilitate continuous decarboxylase inhibition which prolongs the half life of levodopa. For example, results from in vivo studies, as described below, in which L-dopa was administered continuously in parallel with oral administration of carbidopa every 6-8 hours demonstrate a pulsatile pattern of L-dopa plasma levels that coincide with carbidopa oral dosing regimen, but concomitant and/or frequently repeated, e.g., simultaneous dosing of dopa decarboxylase inhibitor (e.g. of carbidopa or a salt thereof, or benserazide) with or without COMT inhibitors with discrete or continuous administration of levodopa is more effective in the treatment of e.g., Parkinson's disease. Further, it has been discovered that the pharmacokinetic profile of, for example, carbidopa (with or without entacapone) supports such new therapies that include substantially continuous administration of dopa decarboxylase inhibitors (e.g. benserazide or carbidopa or a salt thereof) with or without COMT inhibitors together with administration (continuous or at discrete intervals) of e.g. levodopa or a salt thereof.

Provided herein are formulations of carbidopa that unexpectedly allow for stable dissolution of higher concentrations (e.g., greater than 1% by weight) of carbidopa and/or levodopa at e.g. physiologically acceptable pH, for e.g., substantially continuous subcutaneous or transdermal administration. Such formulations may also be suitable for intravenous, intradermal, oral or intraduodenal administration. For example, provided herein are formulations and methods capable of obtaining substantially constant inhibition of dopa decarboxylase activity upon administration, thereby increasing the half life of administered levodopa and substantially reducing the pulsatility of levodopa plasma levels to avoid low trough levels of plasma levodopa.

A treatment strategy of continuous carbidopa administration in accordance with the present invention may simulate L-dopa substantially continuously. For example, therapies and/or methods of the present invention may extend a levodopa oral dosing regimen to about 2 to about 3 times/day, and/or reduce daily dose of levodopa, and/or reduce or even eliminate the risk of motor complications associated with standard oral levodopa formulations in Parkinson's patients.

Compositions

Provided herein, in an embodiment, is a pharmaceutically acceptable formulation that includes a carbidopa salt such as carbidopa arginine, that allows for substantially continuous administration of carbidopa. For example, while carbidopa free base is practically insoluble in alcohol, chloroform or ether and only slightly soluble in water, provided herein, for example, is a stable liquid formulation that includes carbidopa and may be suitable for substantially continuous administration to a patient. Further, such formulations may have a physiologically acceptable pH.

In one aspect, the present invention relates to a carbidopa salt with a basic amino acid selected from arginine, lysine, or histidine. In one preferred embodiment, the salt is the carbidopa arginine salt.

The disclosure also provides, in an embodiment, a liquid formulation comprising a disclosed carbidopa salt. For example, a disclosed carbidopa salt (e.g. carbidopa arginine, carbidopa histidine, carbidopa lysine) may be dissolved in an aqueous solution, (e.g., having a pH of about 6 to 9.5, preferably from about 7 to about 9, more preferably from about 8 to 9 at 25 C or at 30° C. Alternatively, carbidopa (free base) and a basic amino acid salt (e.g. arginine, histidine and/or lysine) are dissolved together in a liquid (e.g. an aqueous liquid) to form a disclosed liquid formulation. Disclosed liquid formulations may include about 1.0% by weight or more carbidopa or carbidopa salt, for example, may include about 1% to about 20% by weight or more carbidopa, e.g., about 2% to about 10% by weight carbidopa. For example, a liquid formulation may include carbidopa and a basic amino acid (such as arginine) in molar ratio of about 1:0.5 to about 1:2.5, or about 1:1 to about a 1:1.2, e.g., about 1:1 or 1:1.1.

Disclosed liquid formulations (e.g. a liquid composition comprising carbidopa and arginine or an arginine salt of carbidopa) may be stable for 24 hours, for 48 hours, for 7 days, or more at 25° C. For example, an exemplary liquid formulation may include a 1:1.1 molar ratio of carbidopa:arginine, with about 2% to about 15%, or about 2% to about 10%, or 2% to about 6% by weight carbidopa. Such a carbidopa:arginine liquid formulation may be more stable at 7 days as compared to a liquid composition that includes a lysine or histidine salt of carbidopa.

In some embodiments, disclosed liquid formulations or compositions are liquid solutions, i.e. are substantially homogenous liquid mixtures. Such liquid mixtures may comprise water and/or other excipients. In another embodiment, disclosed liquid compositions may be substantially non-aqueous.

For example, as disclosed in Example 6, below, a stable liquid solution can be unexpectedly formed from carbidopa and arginine. Such a solution is stable at room temperature, e.g., is a substantially clear solution, even at high carbidopa concentrations of 2, 3, 4, 6, and/or 8 weight percent carbidopa. Such solutions, e.g. up to about 6 weight percent carbidopa, are stable (e.g., no precipitation) at least for 48 hours. Further, because such disclosed solutions, even at high concentrations of carbidopa, have a physiologically acceptable pH, such solutions can be adjusted to an appropriate pH, but still have a significant amount of carbidopa in a smaller volume so that it facilitates patient administration, without e.g. administering large volumes of solution.

Further, solutions having carbidopa and arginine (e.g., the arginine salt of carbidopa) are unexpectedly more stable even as compared to solutions of carbidopa with histidine or lysine, as shown below in e.g. Example 6.

Contemplated liquid formulations may, in some embodiments, further comprise levodopa or levodopa and arginine, and/or optionally a catechol-O-methyl transferase (COMT) inhibitor, such as entacapone or tolcapone; and/or a monoamine oxidase (MAO)-A or MAO-B inhibitor, such as moclobemide, rasagiline, selegiline or safinamide.

Also disclosed herein is a levodopa salt with a basic amino acid selected from the group consisting of arginine, lysine, and histidine, for example, an arginine salt of levodopa. For example, provided herein is a liquid formulation comprising an arginine salt of levodopa, or a liquid formulation comprising arginine and levodopa. In an embodiment, provided herein is a liquid formulation that includes levodopa and arginine in a molar ratio of about 1:1.5 to about 1:2.5, or about 1:1.8 to about 1.20. Such levodopa and arginine formulations or solutions may have a pH of about 8 to about 10, for example, about 8.5 to about 9.5. A disclosed formulation having levodopa and arginine may include about 2%, 3%, 4%, 5%, 6% or more by weight levodopa, e.g., may include about 4% or more by weight levodopa.

In some embodiments, a disclosed liquid formulation will be stable for a period of 1 day, 2 days, 3 days, 1 week, or 1 month or more at room temperature. In an embodiment of the invention, a disclosed liquid formulation further comprises a pharmaceutically acceptable excipient such as e.g., N-methylpyrrolidone (NMP), polyvinylpyrrolidone (PVP), or propylene glycol, or a combination of one or more, and may further comprise one or more antioxidants such as, but not limited to, N-acetyl cysteine, sodium bisulfate, gluthatione, and ascorbic acid. For example, in one embodiment, provided herein is a stable liquid formulation that comprises about 0.5 to about 20% of carbidopa (e.g. about 2% to about 6%), about 1 to about 20% arginine, about 0 to about 30% NMP, about 0 to about 5% PVP, and/or about 0 to about 5% of one or more water soluble antioxidants, by weight.

The invention further provides a stable lyophilized powder comprising a disclosed carbidopa salt e.g., arginine salt. In one embodiment, such stable lyophilized powder may comprise about 20-99% of the carbidopa salt, about 0-60% NMP, about 0-15% PVP, and about 0-5% of one or more water soluble anti oxidants. The lyophilized powder can be reconstituted into a liquid formulation by addition of water alone or water with NMP, and may include or not include antioxidants.

Liquid formulations of the invention may be designed for continuous administration of a carbidopa or levodopa salt to a patient in need thereof. For example, a patient may be substantially continuously administered (e.g. subcutaneously, transdermally, intraduodenally, intradermally, or intravenously) a formulation that includes a disclosed carbidopa salt such as the arginine salt of carbidopa, while levodopa, a levodopa salt, or a composition comprising levodopa is orally administered at discrete intervals, e.g., 2, 3, 4, or 5 times a day.

As used herein in the specification, the term "a composition comprising levodopa" contemplates formulations that comprise levodopa, optionally together with a decarboxylase inhibitor, a catechol-O-methyl transferase (COMT) inhibitor, and/or a MAO-A or MAO-B inhibitor. For example, a composition comprising levodopa includes a dosage formulation that comprises levodopa (or a salt thereof) and optionally another drug, where the dosage formulation may be an immediate release, controlled release, dual release or multiple release formulation suitable for oral administration.

The term "decarboxylase inhibitor" refers to a dopa decarboxylase inhibitor, e.g., a drug that inhibits the peripheral metabolism of levodopa to dopamine by aromatic L-amino acid decarboxylase such as carbidopa and benserazide.

The term "pharmaceutically acceptable carrier" or "pharmaceutically acceptable excipient" as used herein refers to any and all solvents, dispersion media, preservatives, antioxidants, coatings, isotonic and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions.

The term "physiologically acceptable pH" is understood to mean a pH of e.g., a composition that facilitates administration of the composition to a patient without significant adverse effects, e.g. a pH of about 4 to about 9.

COMT inhibitors refer to inhibitors that inhibit the degradation of levodopa to 3-methyldopa by catechol-O-methyl transferase and prolong the action of levodopa, such as entacapone or tolcapone. For example, compositions comprising levodopa contemplated herein may also include a decarboxylase inhibitor (carbidopa or benserazide) and entacapone, e.g. "triple therapy".

MAO-A or MAO-B inhibitors prevent the breakdown of dopamine by monoamine oxidases, e.g., moclobemide, rasagiline, selegiline or safinamide, more preferably, rasagiline.

Also contemplated herein is a kit comprising: a) a first formulation comprising a carbidopa:arginine and/or carbidopa and arginine, wherein said first formulation is suitable for continuous administration; b) a second formulation comprising levodopa or an arginine salt of levodopa, wherein said second formulation is suitable for oral administration; and c) instructions for administration of formulation a) in conjunction with formulation b). The formulation a) comprising the carbidopa salt may be suitable for continuous administration by any suitable route such as transdermally, intravenously, subcutaneously, intradermally, intramuscularly or intraduodenally.

The first formulation of a contemplated kit comprising the carbidopa salt may be liquid or a lyophilized powder that can be reconstituted into a liquid formulation, or, for example, may form part of a transdermal patch, and may be designed for continuous administration by any suitable route such as, but not limited to, transdermally, intravenously, subcutaneously, intradermally, intramuscularly or intraduodenally. In an embodiment, the first formulation comprises a disclosed carbidopa salt and is suitable for administration subcutaneously. The second formulation of a contemplated kit may include the levodopa, a levodopa ester, a levodopa salt, or a composition comprising levodopa, and may be presented as any suitable oral dosage such as, but not limited to, pills, tablets, dispersible tablets, capsules, liquid, and the like. In an embodiment, the second formulation may be in the form of an immediate release, controlled release or dual release oral formulation that comprises both levodopa and benserazide, or both levodopa and carbidopa. Such oral formulation in the form of pills, tablets, or the like, may comprise a ratio of carbidopa or benserazide to levodopa of about 1:10 to 1:4, preferably from about 1:4 to 1:1. Other contemplated second formulations include formulations, e.g., tablets that include levodopa, carbidopa, and entacapone, or e.g. a tablet that includes levodopa arginine salt and/or carbidopa arginine salt.

In another embodiment, the kit comprises a first liquid formulation comprising carbidopa and arginine suitable for, but not limited to, transdermal, intravenous, subcutaneous, intradermal, intramuscular, intraduodenal continuous administration, and a second formulation in the form of an immediate release, controlled release or dual release oral formulation comprising levodopa and carbidopa. The oral formulation in the form of pills, tablets, or the like, may comprise a ratio of carbidopa to levodopa from about 1:10 to about 1:4, preferably from about 1:4 to about 1:1.

In another aspect, the present invention relates to a formulation comprising a carbidopa ester such as, but not limited to, the ethyl, propyl, isopropyl or hexyl ester of carbidopa, and salts thereof. Examples of levodopa esters contemplated herein include the alkyl esters, e.g., the methyl, ethyl, propyl, or isopropyl ester, or the benzyl ester.

Methods

In a further aspect, the present invention provides a method for treatment of a disease or disorder characterized by reduced and/or fluctuating levels of dopamine in a patient's brain, comprising co-administering substantially continuously to a patient in need a therapeutically effective amount of a decarboxylase inhibitor, a salt or an ester thereof, together with a therapeutically effective amount of levodopa or salt thereof or a composition comprising levodopa. As shown in the Examples, separate continuous administration of carbidopa, together with administration of levodopa, even with discrete (e.g. oral) administration of levodopa, to a patient results in significantly higher levels of levodopa in the plasma of a patient upon administration as compared to a current standard of discrete carbidopa and levodopa simultaneous dosing. For example, disclosed methods may result in a half-life of levodopa in the plasma of a patient that is at least 1.5, or at least two times, longer after continuous administration of carbidopa as compared to the half life of levodopa in a patient's serum after administering levodopa without continuous administration of carbidopa (e.g., with discrete, oral administration).

Contemplated administration of e.g., carbidopa and levodopa, following the disclosed methods, typically can be carried out over a defined time period (usually weeks, months or years depending upon the combination selected). Contemplated therapies are intended to embrace administration of multiple therapeutic agents in a manner wherein a dopa decarboxylase inhibitor is administered substantially continuously while levodopa is administered at discrete intervals, as well as administration of contemplated therapeutic agents, or at least two of the therapeutic agents, in a substantially simultaneous manner. Administration can be effected by any appropriate route including, but not limited to, oral routes, intravenous routes, intramuscular routes, intradermal routes, subcutaneously, transdermally, and direct absorption through mucous membrane tissues.

In some embodiments, levodopa can be administered by the same route or by different routes as compared to administration of e.g. a contemplated carbidopa formulation. For example, carbidopa may be administered subcutaneously, e.g., substantially continuously, while levodopa may be administered orally, e.g. at discrete intervals. In an embodiment, a disclosed liquid carbidopa composition (e.g. having carbidopa and arginine) is administered substantially continuously, while an oral composition that includes levodopa (and may also include one or more other active agents such as a dopa decarboxylase inhibitor) is administered at discrete intervals. Alternatively, for example, both levodopa and carbidopa may be administered subcutaneously or transdermally.

The disease or disorder characterized by reduced levels of dopamine in the brain contemplated herein are neurological or movement disorders including restless leg syndrome, Parkinson's disease, secondary parkinsonism, Huntington's disease, Shy-Drager syndrome and conditions resulting from brain injury including carbon monoxide or manganese intoxication. In one preferred embodiment, the disease to be treated is Parkinson's disease.

In preferred embodiments, the contemplated decarboxylase inhibitor is the arginine salt of carbidopa. A disclosed carbidopa/arginine formulation may be administered substantially continuously using e.g. a liquid formulation, for example, via a pump for subcutaneous infusion (insulin pump) at an average rate of about 10-250 µl/hour, preferably about 15-85 µl/hour, in conjunction with oral administration of levodopa, an arginine salt of levodopa, or composition comprising levodopa.

For example, a method for treating a neurological or movement disorder e.g., Parkinson's disease, is provided herein comprising substantially continuously administering to a patient in need thereof a pharmaceutically effective amount of a composition comprising a carbidopa and an amino acid such as arginine, lysine or histidine, and administering a pharmaceutically effect amount of composition comprising levodopa. For example, the composition comprising a carbidopa and arginine may be liquid at room temperature. The disclosed composition may be administered substantially continuously over 12 hours, 1 day, 1 week, or more. The composition comprising levodopa may form all or part of an immediate release, controlled release, or dual release oral formulation comprising levodopa and optionally benserazide or carbidopa, and may be administered 1, 2, 3, or 4 times a day, or more for example, by oral administration (e.g. by tablet).

Also provided herein is a method for treatment of a disease or disorder characterized by reduced levels of dopamine in a patient's brain, (e.g., Parkinson's disease) comprising co-administering substantially continuously to a patient in need a therapeutically effective amount of a disclosed levodopa salt.

The invention now being generally described, it will be more readily understood by reference to the following examples which are included merely for purposes of illustration of certain aspects and embodiments of the present invention, and are not intended to limit the invention in any way.

EXAMPLES

Example 1

Preparation and Characterization of Carbidopa-Arginine Salt

Figure 1B:
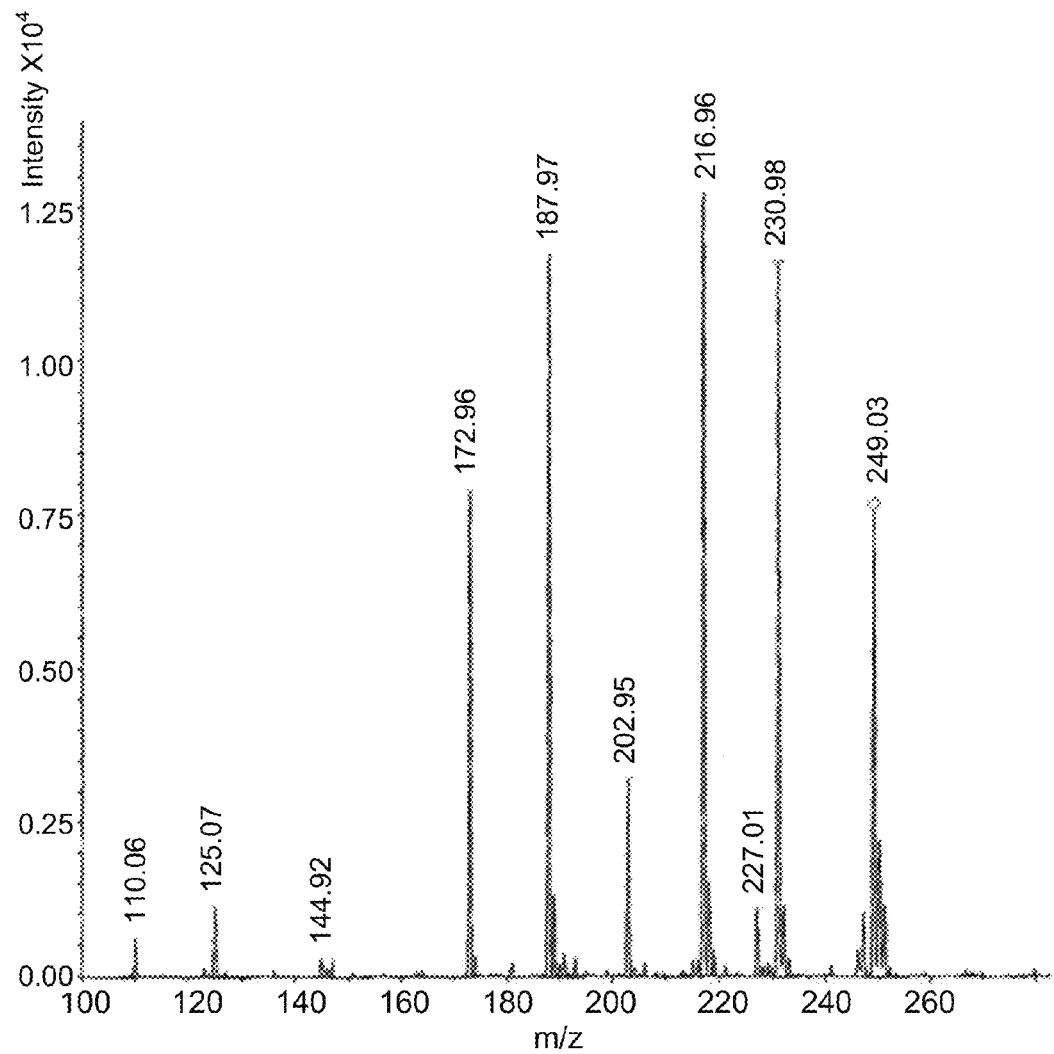
Figure 1C:
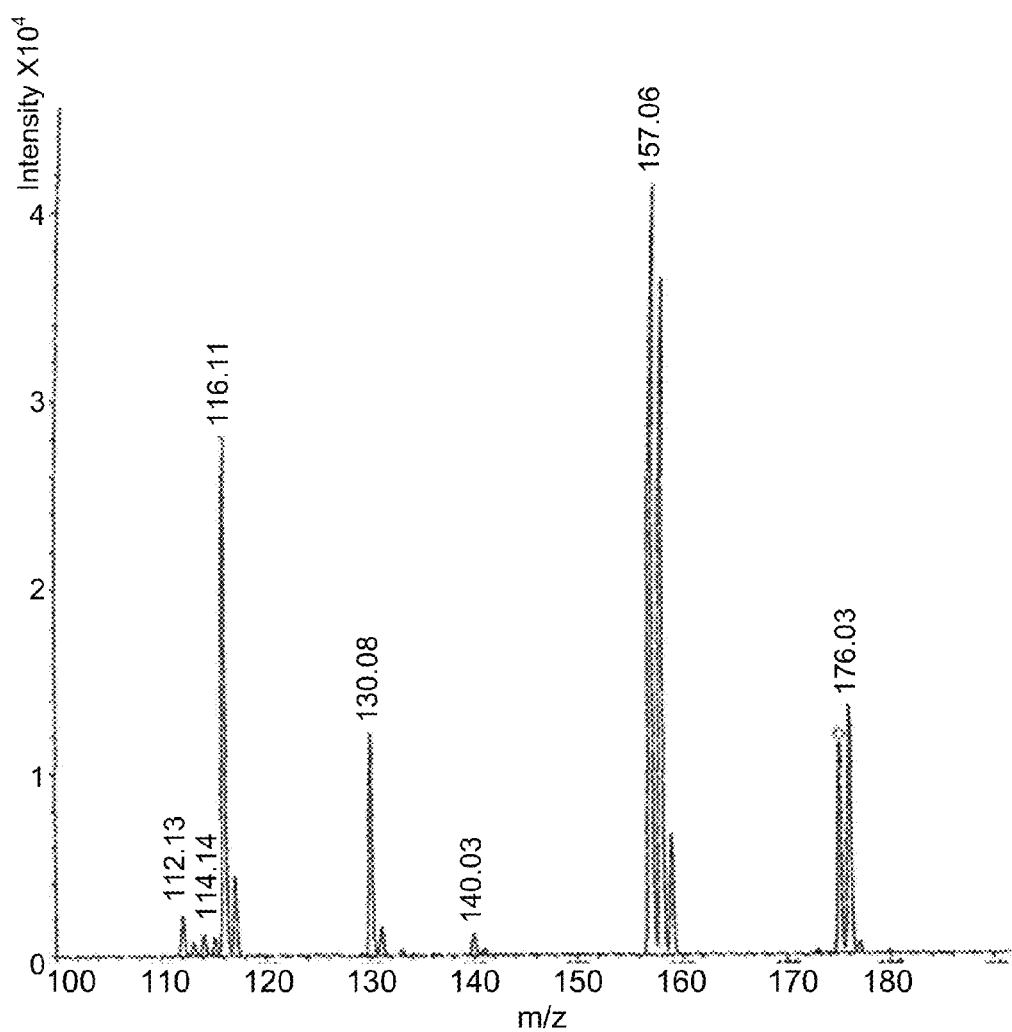

Carbidopa-Arginine salt was prepared as follows:
Carbidopa (CD) [Teva Pharmaceuticals Ltd., Israel] was weighed in a suitable container with L-arginine [Merck] (at molar ratio of 1:1) and a 0.2% sodium bisulfite [Sigma] solution in water was added to obtain a final concentration of 4.0% carbidopa. The mixture was heated to 65±10° C. with constant stirring. When the solids were completely dissolved, solution was filtered using 0.45 µM nylon membrane. The filtered solution was immediately frozen in dry ice and subsequently subjected to lyophilyzation. Off-white crystals were obtained and subsequently subjected to MS analysis. The MS analytical results clearly showed carbidopa and L-arginine ions and fragments (FIG. 1a). Peak 249 represents carbidopa+Na (226+23) with fragments: 227, 188 & 144 (FIG. 1b); Peak 176 represents arginine+2H (174+2) with fragments: 157, 130 & 116 (FIG. 1c).

Example 2

Preparation of Carbidopa Solution/Formulation for Subcutaneous Administration

A 4% Carbidopa solution/formulation was prepared as follows:
Carbidopa [Assia Ltd., Israel] was weighed in a suitable container and water was then added to obtain 73% of the total projected batch weight. Mixture was stirred at room temperature for 20 minutes. L-Arginine [Sigma] was added to the mixture to obtain a molar ratio 1:1 with carbidopa. The mixture was heated to 65±10° C. with constant stirring. When the solids were completely dissolved, N-methyl 2-pyrrolidone [Pharmasolve, ISP] was added to obtain the final concentration of 10% (w/w). Sodium bisulfite [Sigma] solution was prepared and added to obtain a final concentration of 1% (v/w). Stirring was continued for additional 30 minutes at 65±3° C. Thereafter, PVP [Polyvinylpyrrolidone, Sigma] solution was prepared and added to obtain a final concentration of 1% (v/w). Stirring was continued for 30 minutes at 65±3° C. Heating was stopped and the preparation was allowed to cool down to room temperature. Solution was filtered using a sterile 0.22 µM PVDF membrane.

Carbidopa-Arginine solutions/formulations, 2 and 3%, were prepared by diluting the 4% carbidopa-arginine solution/formulation with the respective amount of double distilled water (DDW).

Example 3

Preparation of Carbidopa Solution/Formulation for Subcutaneous Administration

A 6% Carbidopa solution/formulation was prepared as follows:

Carbidopa [Teva] and L-arginine [Merck] (molar ratio 1:1.1) were weighed in a suitable container and water was then added to obtain 84% of the total projected batch weight. N-methyl 2-pyrrolidone [Pharmasolve, ISP] was added to obtain the final concentration of 5% (w/w) Sodium bisulfite [Sigma] solution was prepared and added to obtain a final concentration of 0.1% (v/w). The mixture was heated to 65±10° C. with constant stirring. When the solids were completely dissolved heating was stopped and the preparation was allowed to cool down to room temperature. Solution was filtered using a sterile 0.22 µM PVDF membrane.

Example 4

Preparation of Carbidopa Solution/Formulation for Subcutaneous Administration

A 4% carbidopa solution/formulation was prepared as follows:

Carbidopa [Teva] and L-arginine [Merck] (molar ratio 1:1.1) were weighed in a suitable container and water was added to obtain 89% of the total projected batch weight. N-methyl 2-pyrrolidone [Pharmasolve, ISP] was added to obtain the final concentration of 3.5% (w/w). Sodium bisulfite [Sigma] solution was prepared and added to obtain a final concentration of 0.05% (v/w). The mixture was heated to 65±10° C. with constant stirring. When the solids were completely dissolved, heating was stopped and the preparation was allowed to cool down to room temperature. The solution was filtered using a sterile 0.22 µM PVDF membrane.

Carbidopa-Arginine solutions/formulations, 2 and 3%, were prepared by diluting the 4% Carbidopa-arginine solution/formulation with the respective amount of double distilled water (DDW) containing 3.5% N-MP, with or without 0.05% sodium bisulfite.

Example 5

Preparation of Carbidopa Formulation for Transdermal Delivery

An 8% Carbidopa formulation was prepared as follows:
Carbidopa [Teva] and L-arginine [Merck] (molar ratio 1:1) were weighed in a suitable container and propylene glycol [Merck] was added to obtain 75% of the total projected batch weight. Sodium bisulfite [Sigma] solution was prepared and added to obtain a final concentration of 0.05%. The mixture was heated to 65±10° C. with constant stirring. When the solids were completely dissolved, heating was stopped and the preparation was allowed to cool down to room temperature. PEG-400 [Merck], 10% of the total projected batch weight, was added. The pH was adjusted to 7.5 with 85% lactic acid [Fluka].

Example 6

Preparation and Stability of Carbidopa-Arginine Carbidopa-Lysine and Carbidopa-Histidine Solutions/Formulations Carbidopa solutions/formulations were prepared as follows:

Carbidopa [Teva] was weighed in a suitable container with L-arginine [Merck] or L-lysine [Sigma] or L-histidine [Sigma] (at molar ratio of 1:1, 1:1.1 or 1:2) and water was added. N-methyl 2-pyrrolidone [Pharmasolve, ISP] was added to obtain the final concentration of 5% (w/w). Sodium bisulfite [Sigma] solution was prepared and added to obtain a final concentration of 0.05% (v/w). The mixture was heated to 68±3° C. with constant stirring. When the solids were completely dissolved, heating was stopped and the preparation was allowed to cool down to room temperature. Stable formulations (2% CD:Lysine and 2% CD:Arginine 1:1.1 molar ratio) were further subjected to HPLC analysis at t=0 and t=7 days at 25° C.

The results show the significant difference between the three basic amino acids [L-Arginine (PI-10.76), L-Lysine (PI-9.74) and histidine (PI-7.59)] with respect to their effect on the solubility and stability of carbidopa in aqueous solution: Table 1 indicates the solubility and stability of carbidopa in these aqueous solutions with basic amino acids (arginine, lysine or histidine) as determined visually (Table 1A) or by UV HPLC (Table 1B). With arginine, a stable solution of 6% carbidopa was prepared, whereas a solution with only less than 4% could be formulated with lysine (Table 1A). Furthermore, a solution of 2% carbidopa with lysine was less stable than with arginine after 7 days at 25° C. (Table 1B). In addition, a stable solution with histidine at concentrations≥1% could not be made (Table 1A).

TABLE 1

| | Carbidopa and Arginine Solution | | | | | |
|---|---|---|---|---|---|---|
| | CD Concentration (%) | | | | | |
| | 2 | 4 | 4 | 5 | 6 | 8 |
| Molar Ratio CD:Arginine | 1 to 1 | 1 to 1 | 1 to 1.1 | 1 to 1.1 | 1 to 1.1 | 1 to 1.1 |
| pH of the Solution | 8.2 | 8.2 | 8.4 | 8.5 | 8.7 | 8.9 |

TABLE 1-continued

| Solution Appearance | Clear, slightly yellow | Clear, slightly yellow | Clear, slightly yellow | Clear, slightly yellow | Clear, slightly yellow | Clear, slightly yellow |
|---|---|---|---|---|---|---|
| Stability after 48 h (visual) | Stable | Stable | Stable | Stable | Stable | Precipitated within 24 h |

| Carbidopa and lysine solutions | | | | |
|---|---|---|---|---|
| | CD Concentration (%) | | | |
| | 2 | 4 | 2 | 4 |
| Molar Ratio CD:Lysine | 1 to 1 | 1 to 1 | 1 to 1.1 | 1 to 1.1 |
| PH of the Solution | 8.1 | N/A | 8.2 | 8.23 |
| Solution Appearance | Clear, slightly yellow | Didn't dissolve | Clear, yellow | Precipitated within few minutes |
| Stability after 48 h (visual) | Precipitated after 2 h | N/A | Stable | N/A |

| Carbidopa and histidine solutions | | | | |
|---|---|---|---|---|
| | CD Concentration (%) | | | |
| | 1 | 4 | 2 | 4 |
| Molar Ratio CD:Histidine | 1 to 1.1 | 1 to 1.1 | 1 to 2 | 1 to 2 |
| pH of the Solution | N/A | N/A | 6.7 | N/A |
| Solution Appearance | Didn't dissolve | Didn't dissolve | Clear, white | Didn't dissolve |
| Stability after 48 h (visual) | N/A | N/A | Precipitated after 1 h | N/A |

TABLE 1B

| Amino Acid (AA) | Molar Ratio CD:AA | CD (%) | Time of Analysis | Assay (%) | Impurities Profile (Area %) | | | | |
|---|---|---|---|---|---|---|---|---|---|
| | | | | | 3-OMD | RT 5.3 | RT 12.6 | RT 13.6 | RT 14.5 |
| Lysine | 1:1.1 | 2 | t = 0 | 95.1 | 0 | 3.3 | 0 | 0.50 | 1.07 |
| Arginine | 1:1.1 | 2 | t = 0 | 94.1 | 0 | 4.5 | 0 | 0.41 | 1.05 |
| Lysine | 1:1.1 | 2 | t = 7 d at RT | 70.8 | 0 | N/A | 0 | 1.39 | 26.4 |
| Arginine | 1:1.1 | 2 | t = 7 d at RT | 77.6 | 0 | N/A | 0 | 1.34 | 19.4 |

N/A = Not Applicable

Example 7

Preparation of Levodopa-Arginine Salt

Figure 2A:
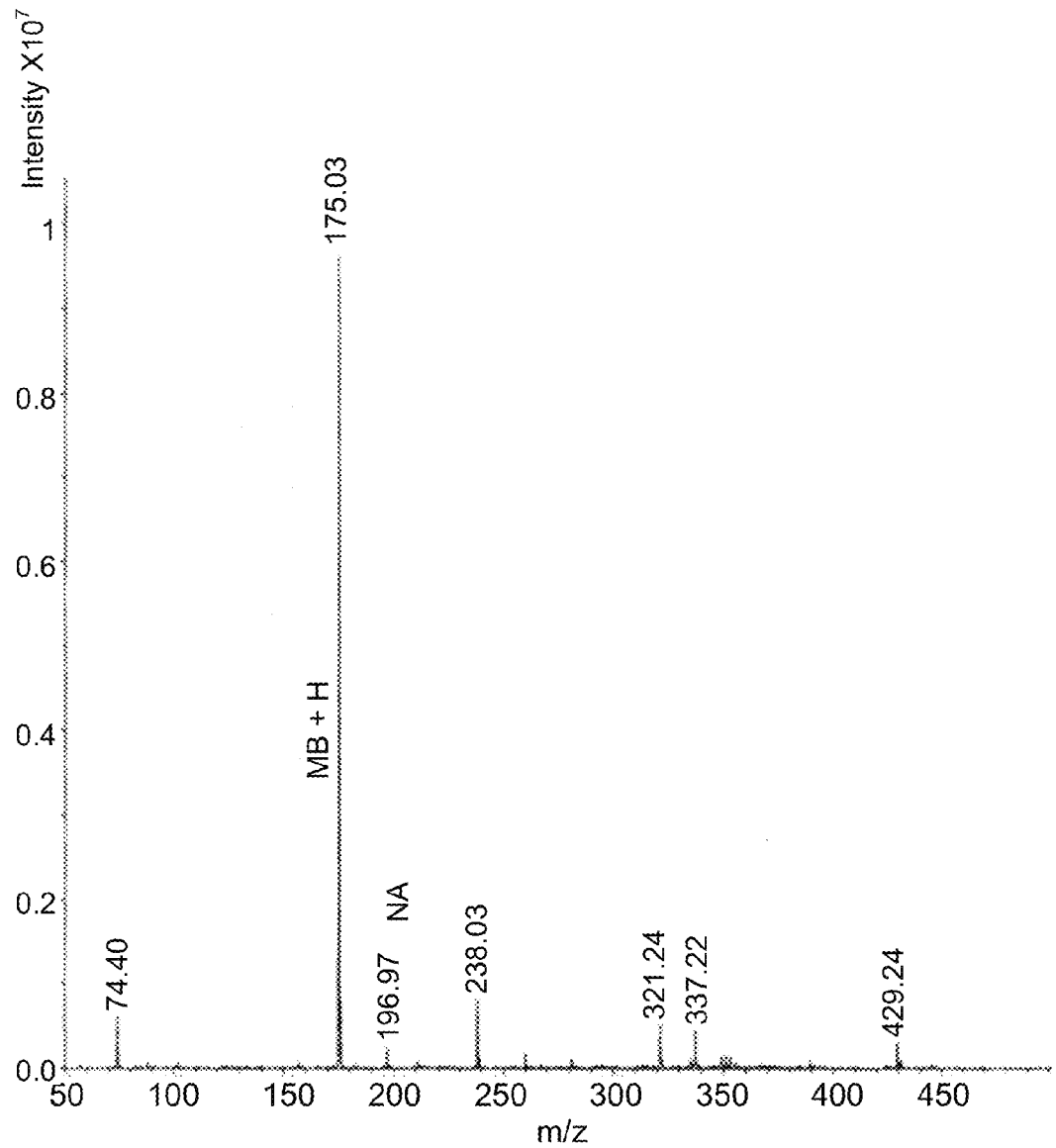
FIGS. 2A-2C depicts the mass spectra of levodopa arginine salt.
Figure 2B:
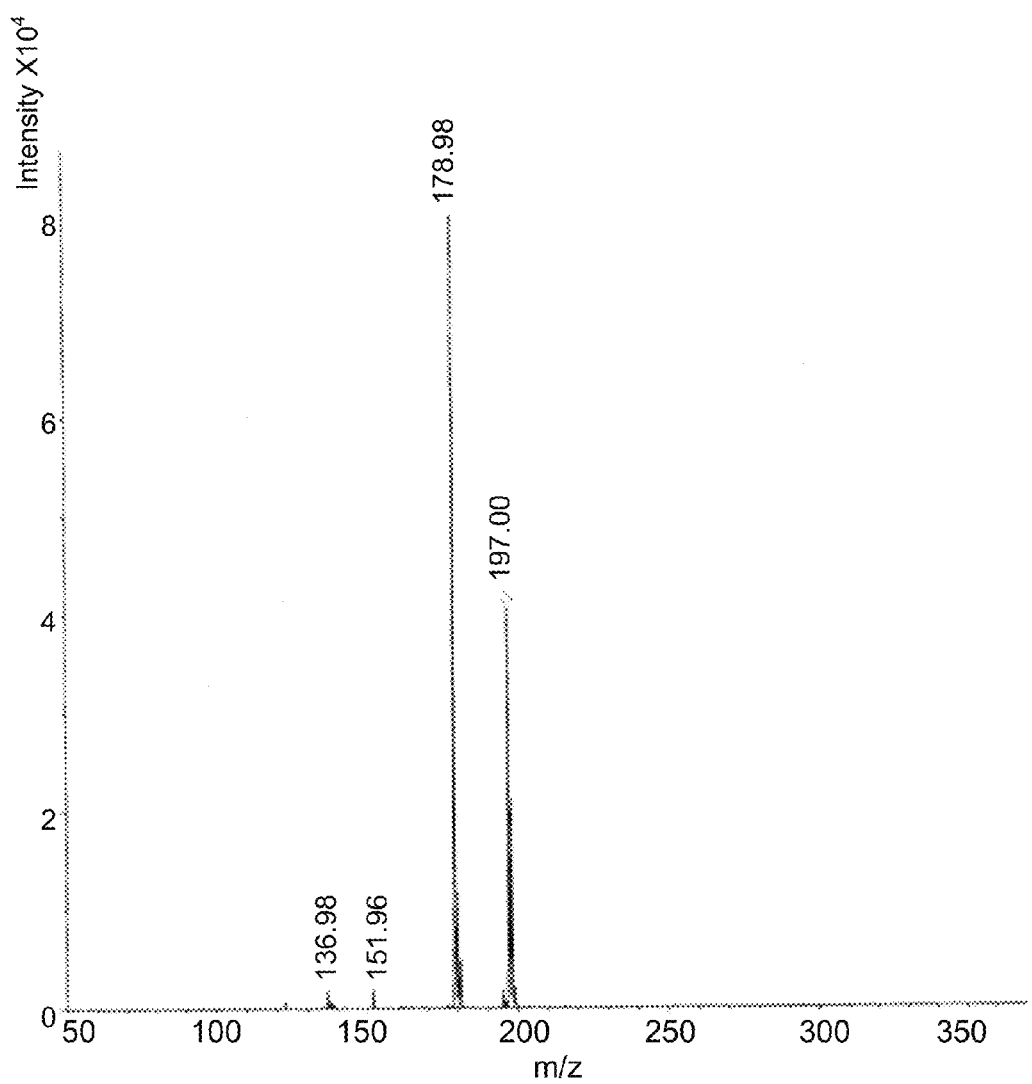
Figure 2C:
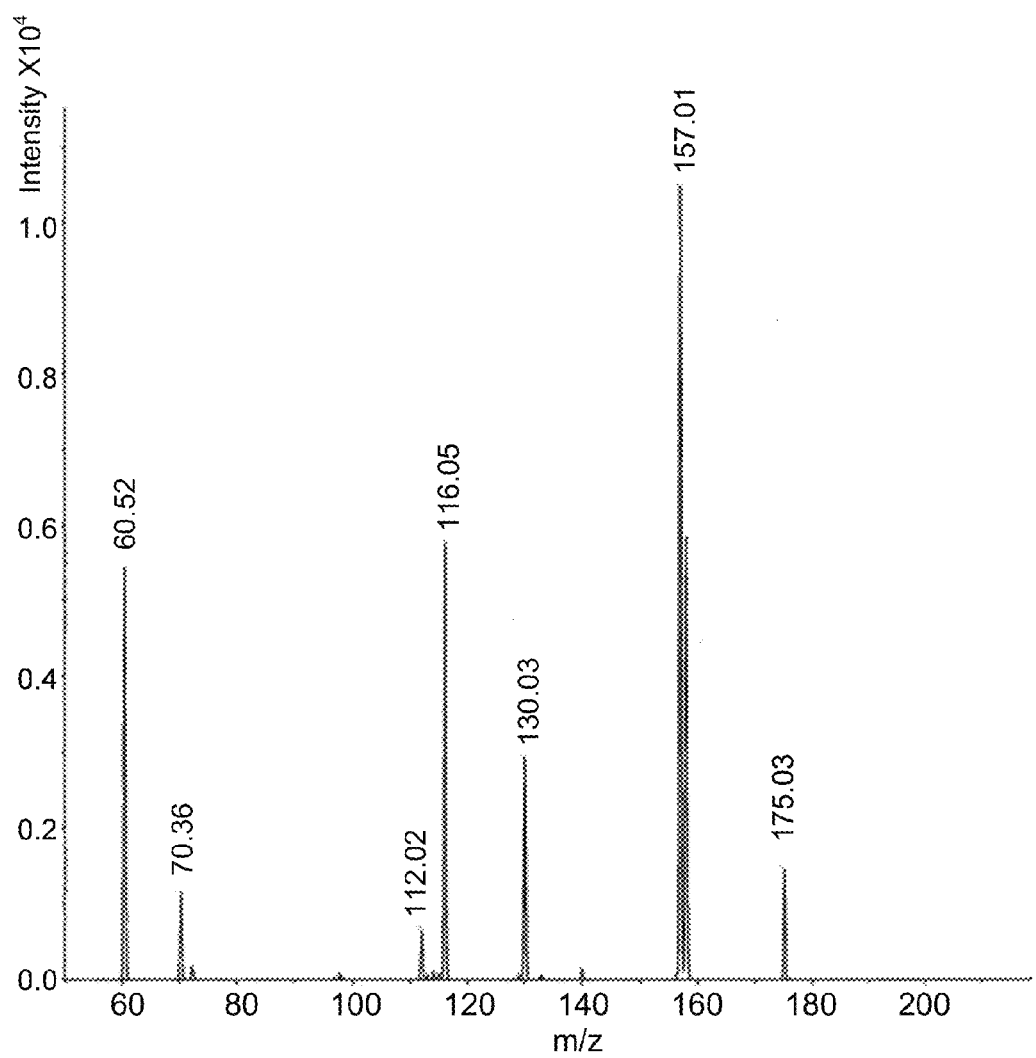

Levodopa-Arginine salt was prepared as follows:

Levodopa (LD) [Teva] was weighed in a suitable container with L-arginine [Merck] (at molar ratio of 1:1.8) and a 0.2% sodium bislfite [Sigma] solution in water was added to obtain a final concentration of 4.4% L-Dopa. The mixture was heated to 65±10° C. with constant stirring. When the solids were completely dissolved, solution was filtered using 0.45 μM nylon membrane. The filtered solution was immediately frozen in dry ice and subsequently subjected to lyophilization. The filtered solution was immediately frozen in dry ice and subsequently subjected to lyophilyzation. Off-white crystals were obtained and subsequently subjected to MS analysis. The MS analytical results (shown in FIG. 2) clearly showed LD and Arginine ions. LD: 197 with fragments 178.97, 151.96, 136.98 (FIGS. 2a & 2b); Arginine: 175 with fragments 130, 116 (FIGS. 2a & 2c)

Example 8

Preparation of Carbidopa and Carbidopa/Entacapone Solutions/Formulations for Subcutaneous Administration, and their Local Safety Evaluation in Pigs A 10% carbidopa and 4/6% carbidopa/entacapone solutions/formulations were prepared as follows:

Carbidopa [Assia Ltd.] was weighed in a suitable container and water was then added to obtain 73% of the total projected batch weight. Mixture was stirred at room temperature for 20 minutes. L-Arginine [Sigma] was added to the mixture to obtain a molar ratio 1:1 with Carbidopa. The mixture was heated to 65±10° C. with constant stirring. When the solids were completely dissolved, N-methyl 2-pyrrolidone [Pharmasolve, ISP] was added to obtain the final concentration of 10% (w/w). Sodium bisulfite [Sigma] solution was prepared and added to obtain a final concentration of 1% (v/w). Stirring was continued for additional 30 minutes at 65±3° C. Thereafter, PVP [Polyvinylpyrrolidone, Sigma] solution was prepared and added to obtain a final concentration of 1% (v/w). Stirring was continued for 30 minutes at 65±3° C. Heating was stopped and the preparation was allowed to cool down to room temperature. Solution was filtered using a sterile 0.22 μM PVDF membrane. The filtered solution was immediately frozen in dry ice and subsequently subjected to lyophilization. Lyophilized crystals were re-constituted with double distilled water to obtain 4 and 10% carbidopa solutions. Entacapone [extracted from Comtan®, Novartis] was added to the 4% carbidopa solution to obtain a final concentration of 6% (w/v). Both formulations (10% CD and 4/6% CD/E) were continuously administered sc to pigs for a period of 21h to evaluate potential local reactions. Macroscopic and microscopic evaluations indicated that 21h continuous subcutaneous administration of these carbidopa solutions/formulations was safe. (Table 2).

Table 2 indicates the results of a histological evaluation of skin biopsies obtained from female Landrace×large white swine following continuous subcutaneous administration of 10% CD (carbidopa) or 4/6% CD/entacapone for a period of 21h, at a rate of 25 or 82 μl/h.

TABLE 2

| Infusion Rate | Pig #1 | | | | Pig #2 | | | |
|---|---|---|---|---|---|---|---|---|
| | L CD 10% | | R CD/Ent 4/6% | | L CD/Ent 4/6% | | R CD 10% | |
| | Pod Activation (h) | | | | | | | |
| 25 μl/hr | 21 h | | — | | 21 h | | — | |
| 82 μl/hr | — | | 21 h | | — | | 21 h | |
| Parameter | Histological Observation (Time post patch removal) | | | | | | | |
| | 0 | 10 d | 0 | 10 d | 0 | 10 d | 0 | 10 d |
| Lesion Localization | Subcutis | No Lesions | No Lesions | No Lesions | No Lesions | No Lesions | Subcutis | No Lesions |
| Distribution | Perivascular | | | | | | Perivascular | |
| Inflammation Grade | 0-1 | | | | | | 0-1 | |
| Predominant Cell Type | N | | | | | | N | |
| Necrosis | — | | | | | | — | |
| Fibrosis | — | | | | | | — | |

Key: Localization: Epidermis, dermis, subcutis; _Distribution: Diffuse, multifocal, perivascular; Inflammation Scoring Grade: 0-no inflammation, 1-very mild, 2-moderate, 3-severe; Predominant Cell Type: lymphocytes (L), macrophages (M), neutrophils (N); Necrosis: Yes/No; Fibrosis: Yes/No Example 9

The Effect of Continuous Subcutaneous Carbidopa Administration on the Pharmacokinetic Profile of Levodopa and Carbidopa in Pigs In this experiment, the purpose was to determine the effect of continuous subcutaneous administration of carbidopa, with co-administration of oral L-dopa/carbidopa, on the pharmacokinetics of levodopa in pigs. Pigs weighing 30-35 kg were administered orally with either Stalevo® (Novartis, 100/25/200 mg, LD/CD/E), Dopicar® [Teva]+Lodosyn® (Merck & Co) (125/25 mg, LD/CD) or Sinemet CR® (MSD, 100/25 mg, LD/CD) thrice or twice daily (q8 or 12 h, respectively) with or without carbidopa (60 mg/pig/d) for a total period of 68 h. Blood samples were collected at pre-determined time points and plasma levels of L-dopa and carbidopa were analyzed by LC-MS.

Figure 3A:
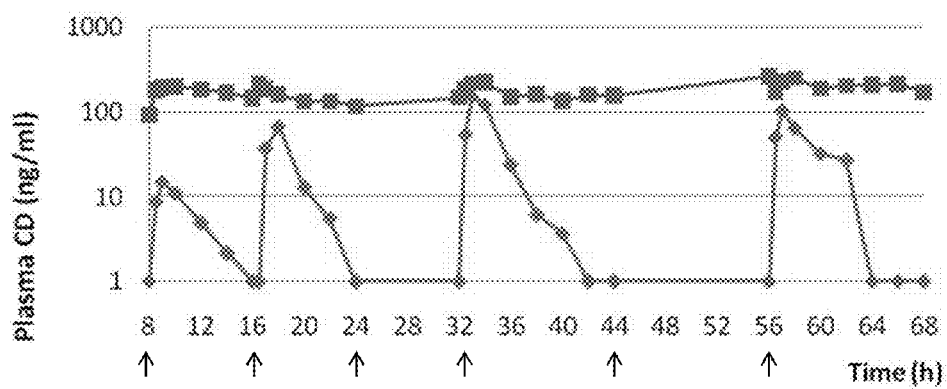
FIGS. 3A-3C show the mean levels of carbidopa determined in plasma of female Landrace×large white swine (30-35 kg) following oral administration of (#A) Stalevo (100/25/200 mg, LD/CD/E), (3B) Dopicar+Lodosyn (125/25 mg LD/CD), (3C) Sinemet CR (100/25 mg, LD/CD) q8 and 12 h, with (squares) or without (diamonds) continuous subcutaneous administration of 3% carbidopa solution.
Figure 3B:
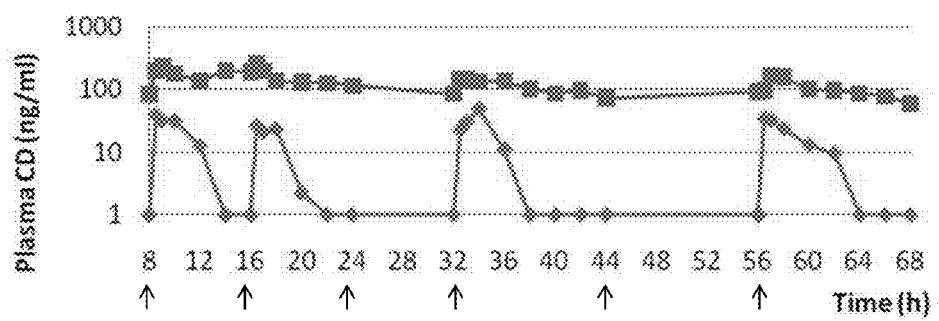
Figure 3C:
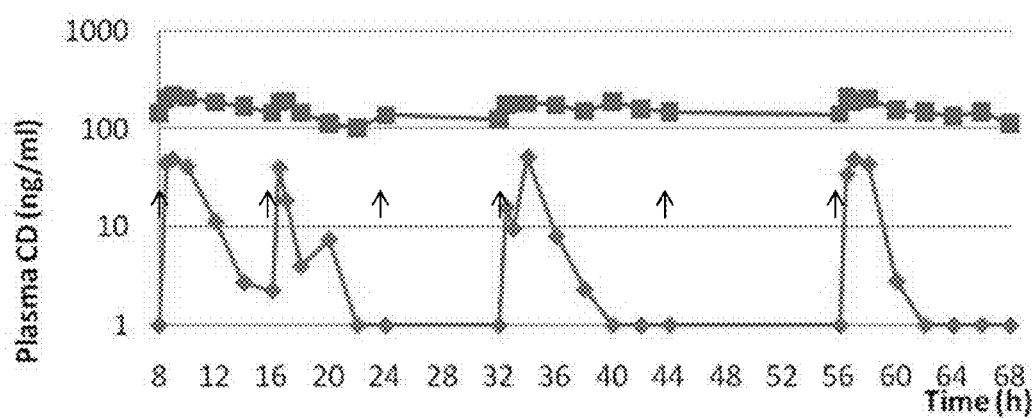

Results showed that the co-administration of continuous subcutaneous carbidopa with any oral LD preparation significantly increases (more than ×2) the half live (VA) and AUC of levodopa. In contrast, increased carbidopa oral dose or frequency did not considerably improve the PK profile of levodopa, as shown in Table 3. Also, constant, steady-state, levels of CD was maintained at 164±34 ng/ml during the 68 hours of continuous SC administration of carbidopa (60 mg/pig/day). This was in opposition to the fluctuating pattern and very low trough levels of CD obtained after administration of standard treatment (FIG. 3). No signs of treatment related local or systemic toxicity were observed throughout the entire 68 h study period.

The pharmacokinetic parameters of levodopa determined in plasma of female Landrace×large white swine (30-35 kg) following oral administration of (A) Stalevo (100/25/200 mg, LD/CD/E), (B) Dopicar+Lodosyn (125/25 mg LD/CD), (C) Sinemet CR (100/25 mg, LD/CD) q8 and 12 h (q8 h=every 8 hours), with or without continuous subcutaneous (SC) administration of 3% carbidopa (CD) solution, with results depicts in Table 3:

TABLE 3

| A. | | | | | |
|---|---|---|---|---|---|
| | Oral Treatment Stalevo (100/25/200 mg) PK Parameters | | | | |
| SC Treatment | $C_{max}$ | $T_{max}$ | $T_{1/2}$ | $AUC_{0-8}$ | $AUC_{0-\infty}$ |
| Without SC CD (n = 8) | 2392 ± 1363.9 | 2.3 ± 0.89 | 1.4 ± 0.30 | 8109 ± 4145.2 | 8309 ± 4265.2 |
| With SC CD (n = 12) | 2355 ± 1157.1 | 2.1 ± 1.00 | 2.9 ± 0.41 | 17527 ± 8470.8 | 19330 ± 8284.8 |
| Significance* (p) | NS | NS | 2E−08 | 0.005 | 0.001 |

| B. | | | | | |
|---|---|---|---|---|---|
| | Oral Treatment LD/CD (125/25 mg) PK Parameters | | | | |
| SC Treatment | $C_{max}$ | $T_{max}$ | $T_{1/2}$ | $AUC_{0-8}$ | $AUC_{0-\infty}$ |
| Without SC CD (n = 7) | 2472 ± 735.6 | 0.9 ± 0.53 | 1.1 ± 0.22 | 7200 ± 3093.2 | 7302 ± 3071.3 |

TABLE 3-continued

| | | | | | |
|---|---|---|---|---|---|
| With SC CD (n = 14) | 4050 ± 1369.5 | 0.8 ± 0.43 | 2.5 ± 0.43 | 17922 ± 4375.7 | 19230 ± 4625.5 |
| Significance* (p) | 0.005 | NS | 1E−07 | 7.4E−06 | 3.3E−06 |

C.

Oral Treatment
Sinemet CR (100/25 mg)
PK Parameters

| SC Treatment | $C_{max}$ | $T_{max}$ | $T_{1/2}$ | $AUC_{0-8}$ | $AUC_{0-\infty}$ |
|---|---|---|---|---|---|
| Without SC CD (n = 8) | 1691 ± 556.2 | 0.9 ± 0.52 | 1.2 ± 0.19 | 4792 ± 1190.8 | 4929 ± 1196.6 |
| With SC CD (n = 15) | 2830 ± 929.2 | 1.2 ± 0.92 | 2.6 ± 0.46 | 12688 ± 3516.3 | 13505 ± 3344.4 |
| Significance* (p) | 0.002 | NS | 3.2E−08 | 2.3E−06 | 3.6E−07 |

*Using one tailed distribution equal variance T-Test

Example 10

The Effect of Continuous Subcutaneous Administration of Carbidopa on Brain Distribution of Levodopa and Dopamine in Mice In this experiment, the purpose was to determine the effect of continuous subcutaneous administration of carbidopa (15 mg/kg/d) on the levels of levodopa and dopamine in the brain following oral administration of levodopa/carbidopa (32/8 mg/kg TID) in mice.

Mice were implanted subcutaneously with Alzet pumps containing Saline (Negative Control), Vehicle or Carbidopa solution. A day following implantation LD/CD was administered orally q8 h. The level of levodopa and dopamine in the brain was determined following the 4$^{th}$ oral dose of LD/CD. The results showed dopamine levels seven hours post-administration of oral LD to be significantly higher in the brains of mice continuously administered SC with carbidopa (FIG. 4A), concurrently with higher levels of plasma LD (FIG. 4B).

Example 11

Dose Effect of Continuous Subcutaneous Carbidopa Administration on Local Toxicity and Pharmacokinetic Profile of Levodopa and Carbidopa in Pigs In this experiment, the purpose was to determine the dose effect of carbidopa continuously administered subcutaneously to pigs on local tolerance and the pharmacokinetics of L-dopa.

Pigs weighing 30-35 kg were administered orally with Sinemet® (Merck & Co., 100/25 mg, LD/CD), thrice daily (q8 h), or Dopicar® (Teva)+Lodosyn® (Merck & Co., (125/25 mg LD/CD), twice daily (q12 h), with continuous subcutaneous vehicle, 2% or 4% carbidopa (0, 40 or 80 mg/pig/d, respectively) for a total period of 24 h. Blood samples were collected at pre-determined time points and plasma levels of L-dopa and carbidopa were analyzed by LC-MS. Skin biopsies were collected from the infusion sites immediately, 1 and 2 weeks post-administration and local tolerance was evaluated by histological analysis of H&E stained slides. No histological treatment-related abnormalities were observed at the sites of infusion.

Figure 5A:
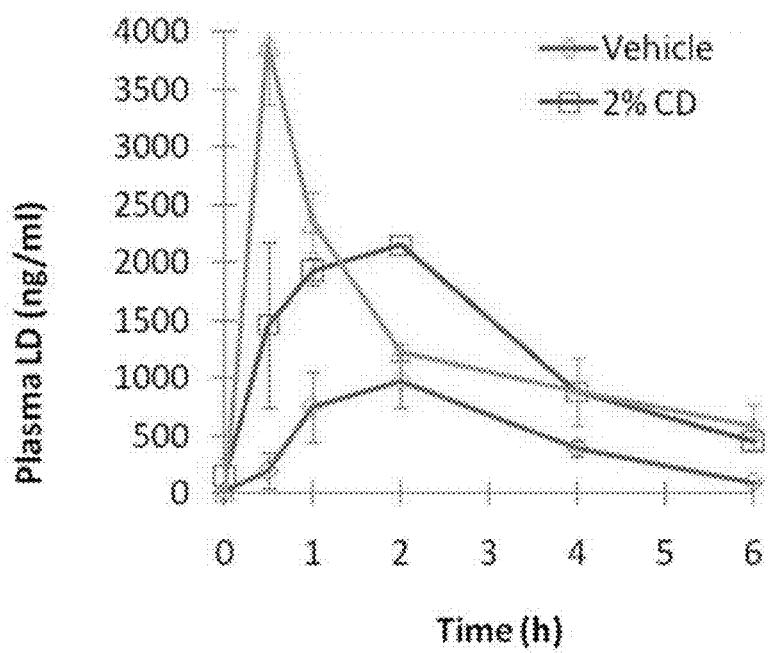
FIGS. 5A-5B depicts mean level of L-Dopa (5A) and carbidopa (5B) determined in plasma of female Landrace×large white swine (30-35 kg) following continuous subcutaneous administration of 0, 2 and 4% carbidopa with oral administration of Sinemet® (100/25 mg) q8 h.
Figure 5B:
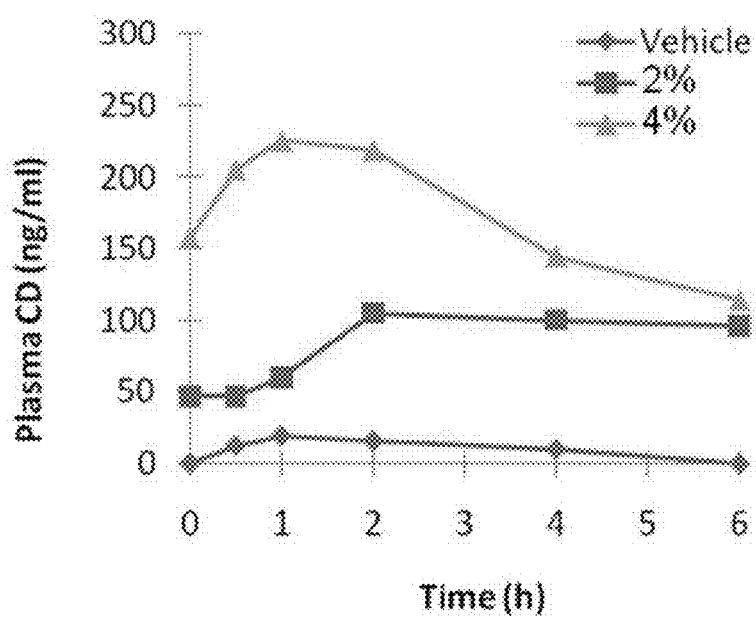
Figure 6A:
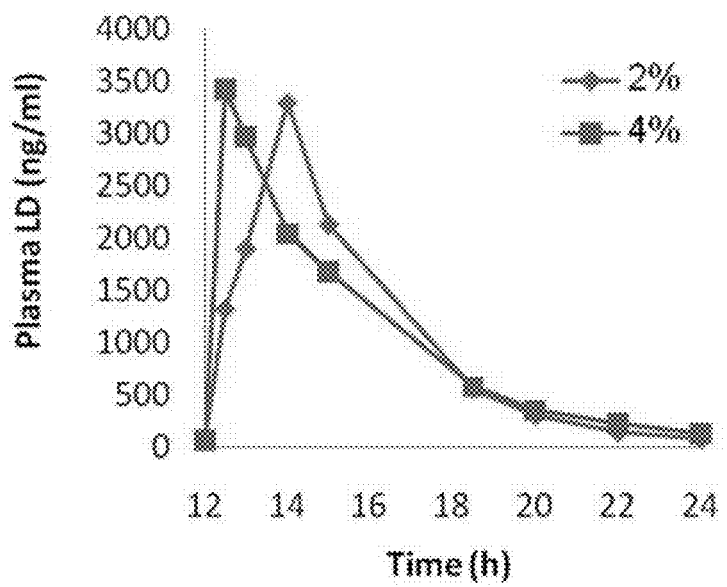
FIGS. 6A-6B depict mean levels of dopa determined in plasma of two female Landrace×large white swine (30-35 kg) (6A, Pig #3; 6B, Pig #4) following continuous subcutaneous administration of 2 and 4% carbidopa with oral administration of Dopicar® (125/12.5 mg LD/CD)+Lodosyn® (12.5 mg CD) q12 h.
Figure 6B:
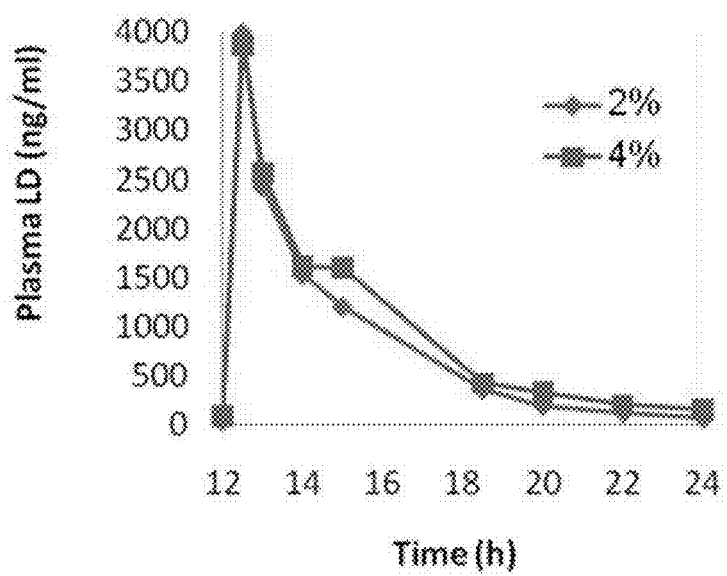

No significant dose effect on the plasma levels of L-dopa was observed when 2 or 4% carbidopa solutions were co-administered with Sinemet® (FIG. 5) or Dopicar®+Lodosyn® (FIG. 6). Thus, under the experimental conditions employed, it was suggested that continuous subcutaneous administration of 2% carbidopa, or less, may be sufficient to maintain optimal inhibition of DDC (dopa decarboxylase) in pigs.

Example 12

Figure 8A:
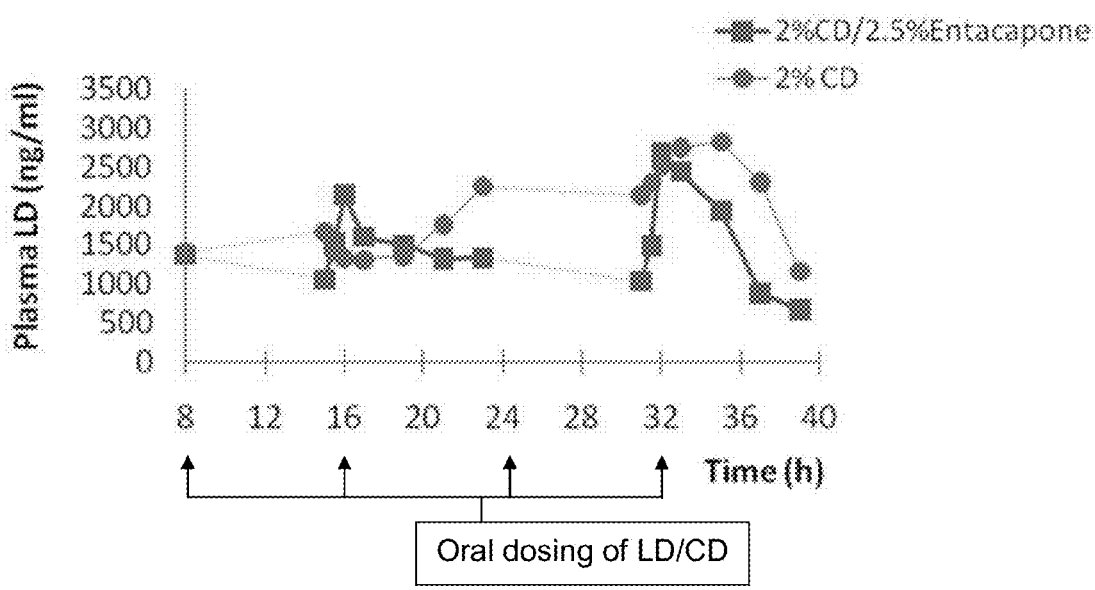
FIGS. 8A-8B depict plasma levels of (8A) L-dopa and (8B) 3-O-methyldopa (3-OMD) as determined in plasma of female Landrace×large white swine (30-35 kg) following continuous subcutaneous administration of 2% carbidopa, with or without 2.5% entacapone, and oral administration of L-dopa/Carbidopa (LD/CD).
Figure 8B:
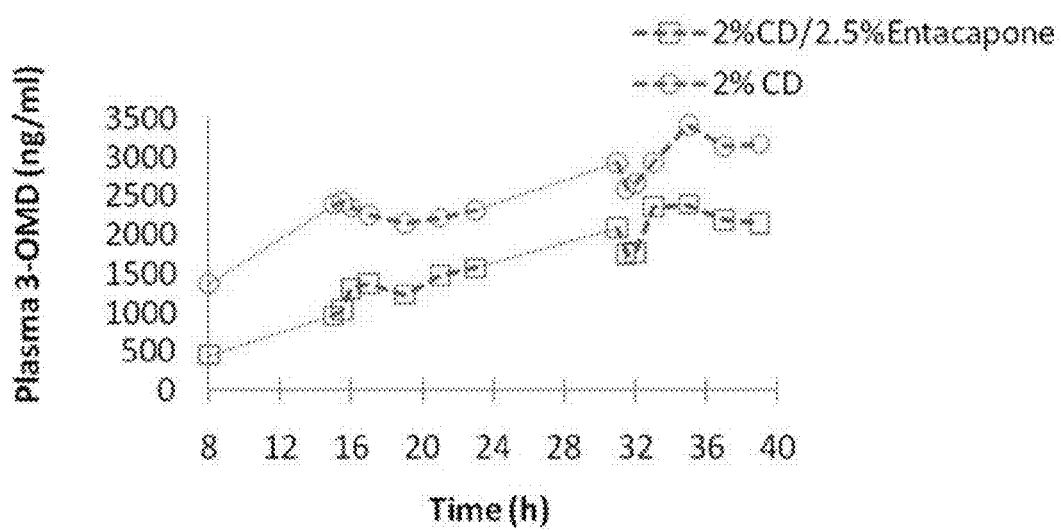

The Effect of Continuous Subcutaneous Administration of Carbidopa, with and without Continuous Subcutaneous Administration of Entacapone, on the Pharmacokinetics of Levodopa in Pigs In this experiment, the purpose was to determine the plasma levels of L-dopa, following continuous subcutaneous administration of carbidopa, with or without entacapone, concomitantly with oral administration of L-dopa/carbidopa in pigs. Plasma levels of L-dopa were measured by HPLC-ECD. The results in FIG. 8 show that entacapone effectively reduced the levels of 3-OMD (3-ortho-methyldopa) (8B), but it did not further extend the pharmacokinetics of levodopa (8A), suggesting that entacapone and/or COMT inhibition interferes with carbidopa/DDC-dependent, or other, LD metabolic pathways.

Example 13

The Effect of Continuous Subcutaneous Administration of Benserazide on the Pharmacokinetics of Levodopa in Pigs In this experiment, the purpose was to determine the plasma levels of L-dopa, following co-administration of oral L-dopa/Carbidopa with continuous subcutaneous administration of another DDC inhibitor, benserazide. Plasma levels of L-dopa were measured by HPLC-ECD.

Figure 7:
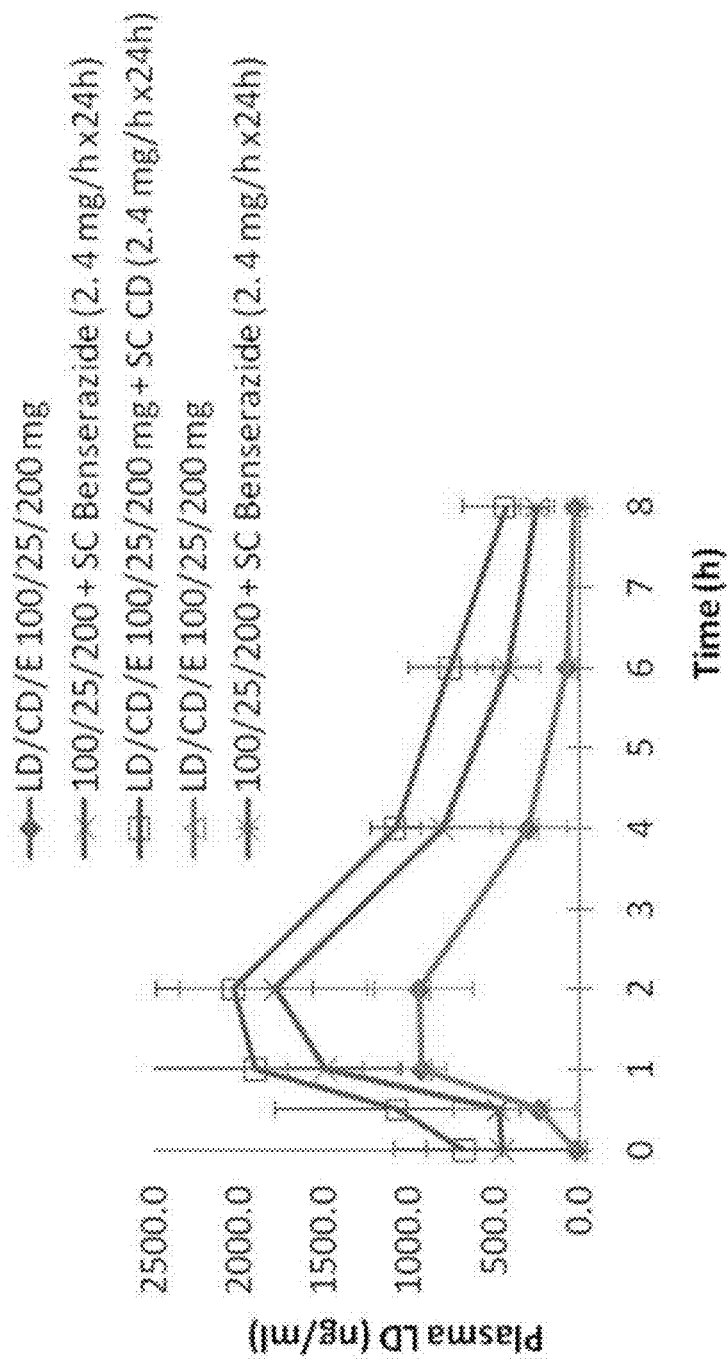
FIG. 7 shows the mean (±SD) LD (levodopa) concentrations (ng/ml) as determined in plasma of female Landrace×large white swine (30-35 kg) following oral administration of Stalevo (LD/CD/E 100/25/200), q8 h, with or without continuous subcutaneous benserazide or carbidopa (60 mg/day).

The results showed that benserazide extended the pharmacokinetic profile of LD, suggesting that continuous dopa-decarboxylase (DDC) inhibition, by any DDC inhibitor, increases the elimination half life of LD, as shown in FIG. 7.

Example 14

Figure 9:
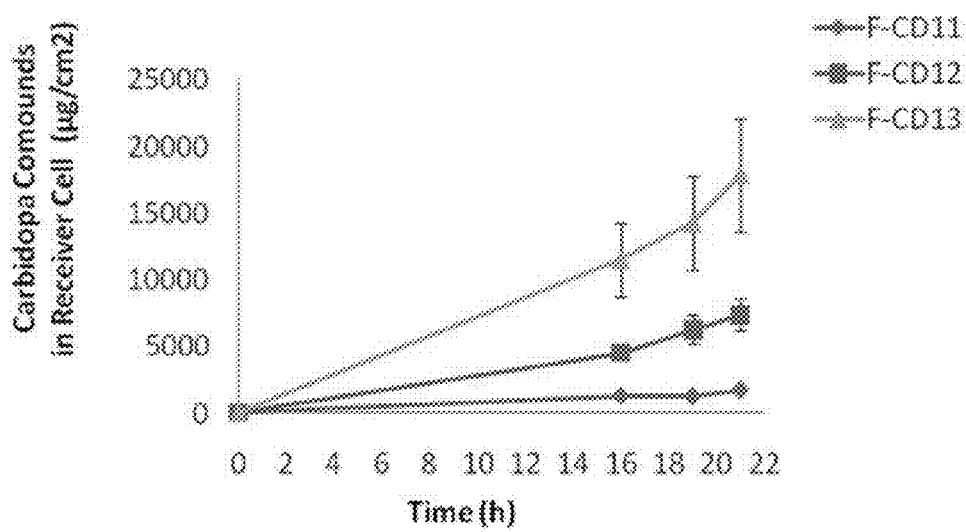
FIG. 9 shows the results of transdermal delivery of carbidopa propyl ester (CDPE).

The Transdermal Delivery of Carbidopa Propyl Ester (CDPE) Through Full Thickness Pig Skin Ex Vivo Using the Franz Cell Delivery System In this experiment, the purpose was to determine the transdermal delivery of carbidopa propyl ester through a full thickness porcine skin, ex vivo using the Franz cell delivery system. Gel formulations containing CDPE were prepared. Samples were collected from the receiver cell at time 0, 16, 19 and 22 hours after formulation application on to the skin. The amount of CD compounds in the receiver cell fluid was determined by a spectrophotometer at 280 nM. The results shown in FIG. 9 demonstrate that CDPE penetrates the skin in an enhancer-dose dependent manner.

Example 15

The Effect of Oral Administration of Levodopa Arginine and Carbidopa Arginine Salts on the Pharmacokinetic Profile of Levodopa and Carbidopa In this experiment, the purpose was to determine the pharmacokinetics of LD and CD administered orally as arginine salts, either enteric-coated or not. Pigs were orally administered with 255/45 mg LD-arginine salt (LDs)/CD-arginine salt (CDs) to 30-35 kg pigs in gelatin coated or non-coated capsules (corresponding to 100/25 LD/CD). Plasma levels of LD and CD were measured by HPLC-ECD.

Figure 10A:
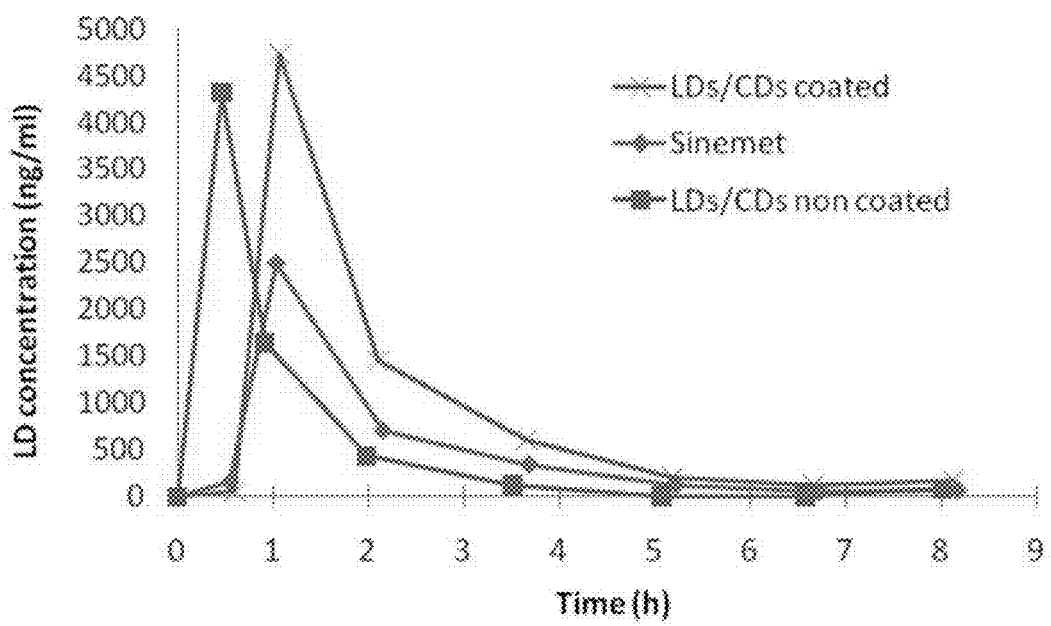
FIGS. 10A-10B depict plasma levels of (10A) levodopa and (10B) carbidopa as determined in plasma of female Landrace×large white swine (30-35 kg) following oral administration of enteric coated or uncoated LD and CD as arginine salts (designated LDs and CDs, respectively, 100/25 mg LD/CD) as compared to Sinemet (100/25 mg LD/CD).
Figure 10B:
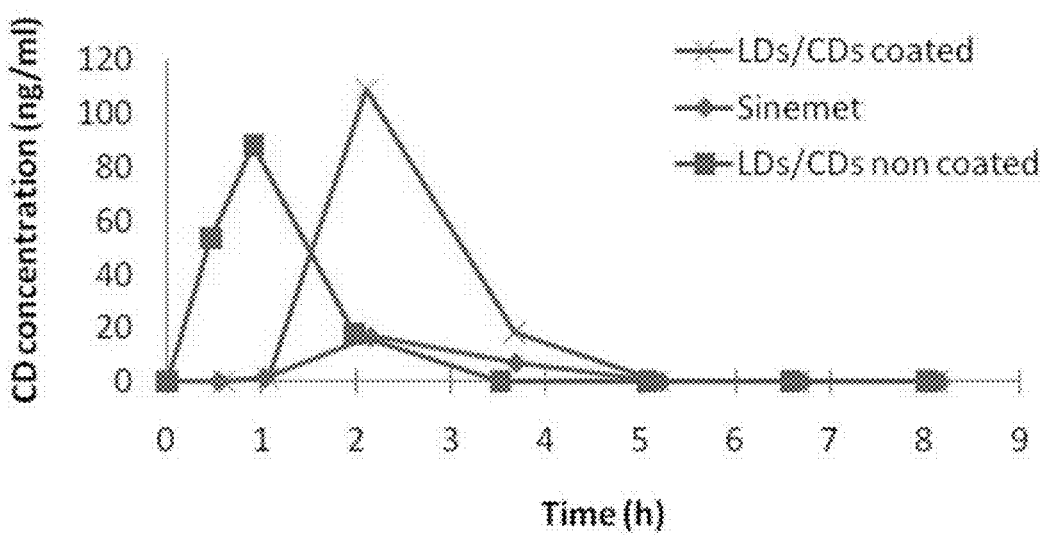

The results showed that LDs and CDs were absorbed more rapidly and efficiently as compared to LD/CD (Sinemet®), and that oral administration of enteric coated LDs/CDs extended the PK of plasma LD (FIG. 10A) and CD (FIG. 10B).

Example 16

The Inhibitory Effect of Carbidopa Esters on the Activity of Dopa-Decarboxylases (DDC) In Vitro In this experiment, the purpose was to determine the inhibitory effect of carbidopa esters (CDEs) on the activity of dopa-decarboxylases. DDC enzymes were obtained from porcine liver homogenate and their activity was measured by comparing LD concentrations with and without carbidopa propyl ester (CDPE). Liver homogenate preparation was based on the method described by Umezawa et al; (J. Antib. 1975, 28(12):947-52).

All samples were separated on high pressure liquid chromatography columns and the identity and concentration of L-dopa and dopamine were determined by HP UV-HPLC analysis at 280 nM.

Figure 11:
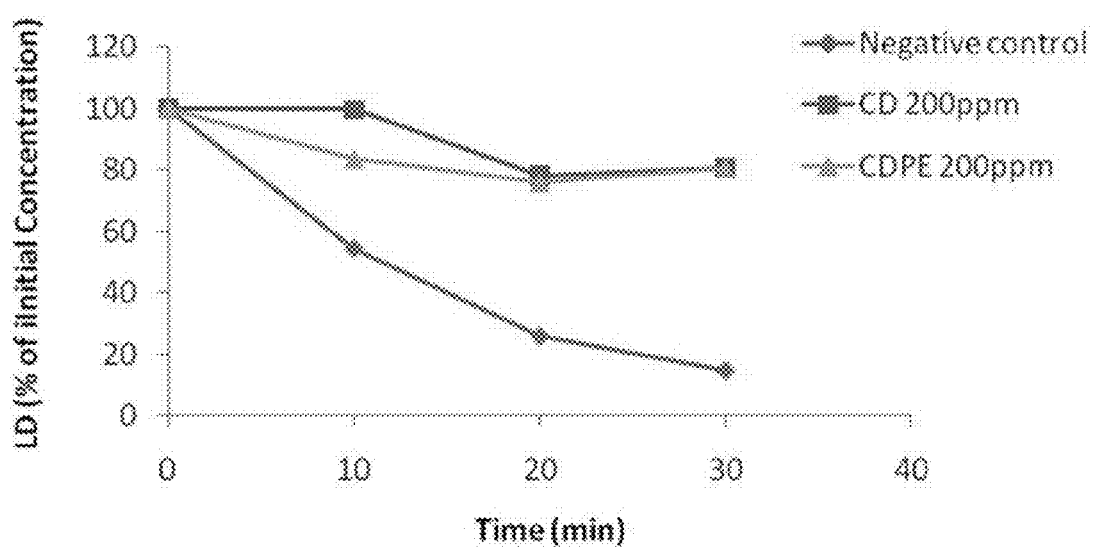
FIG. 11 depicts the inhibition of L-dopa decarboxylation by carbidopa and carbidopa propyl ester.
Figure 12A:
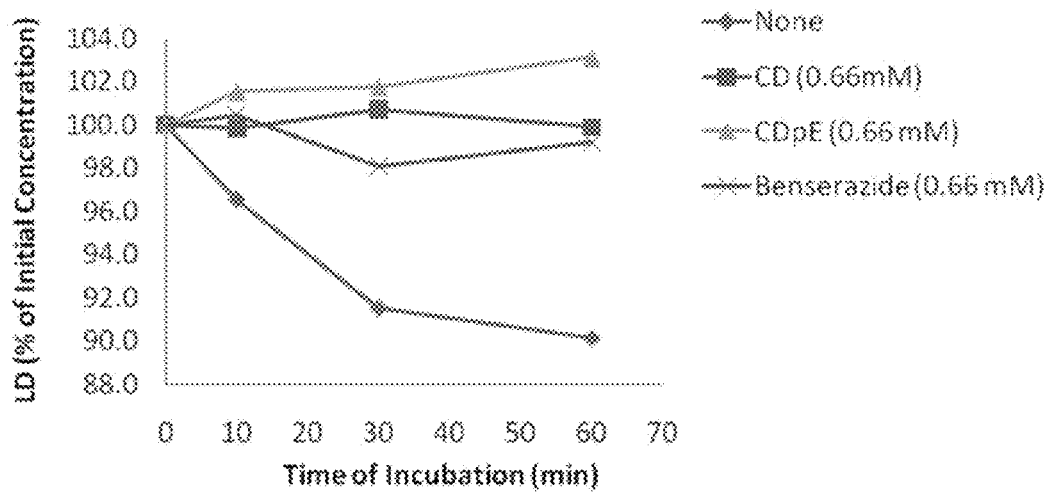
FIGS. 12A-12B depict (12A) the inhibition of L-dopa decarboxylation and the metabolism of L-dopa to dopamine (12B) by carbidopa and carbidopa propyl ester in liver extract.
Figure 12B:
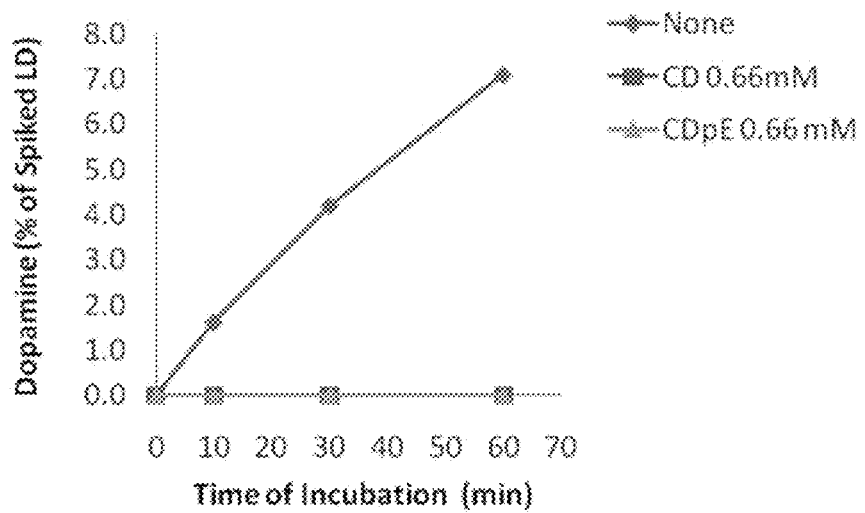

The results shown in FIGS. 11 and 12 demonstrate that CDPE inhibits the decarboxylation of L-dopa to dopamine, in a similar manner to carbidopa and benserazide.

EQUIVALENTS

While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present invention.

INCORPORATION BY REFERENCE

The entire contents of all patents, published patent applications, websites, and other references cited herein are hereby expressly incorporated herein in their entireties by reference.

The invention claimed is:

1. A pharmaceutically acceptable liquid composition comprising levodopa, arginine, and about 2% to about 6% by weight carbidopa, wherein the pH of the liquid composition is 8 to 10 at 25° C.

2. The pharmaceutically acceptable liquid composition of claim 1, wherein the pH is about 9.5 at 25° C.

3. The pharmaceutically acceptable liquid composition of claim 1, comprising about 3% by weight carbidopa.

4. The pharmaceutically acceptable liquid composition of claim 3, further comprising a water-soluble anti-oxidant.

5. The pharmaceutically acceptable liquid composition of claim 4, wherein said water-soluble antioxidant is selected from the group consisting of ascorbic acid, N-acetylcysteine, and a combination thereof.

6. The pharmaceutically acceptable liquid composition of claim 1, comprising at least 6% by weight levodopa.

7. The pharmaceutically acceptable liquid composition of claim 1, wherein the liquid composition has no precipitation when held for 48 hours at room temperature.

8. The pharmaceutically acceptable liquid composition of claim 1, wherein when the liquid composition is stable for a period of 1 day, 2 days, 3 days, 1 week, or 1 month or more at room temperature.

9. The pharmaceutical composition of claim 1, wherein said composition is suitable for intravenous, oral, or intraduodenal administration.

10. A method of treating a disease or disorder characterized by reduced levels of dopamine in a patient's brain, comprising administering to said patient an amount of a composition of claim 1 in an amount effective to treat said disease or disorder.

11. The method of claim 10, wherein said administering is intravenous, oral, or intraduodenal.

12. The method of claim 11, wherein said administration is substantially continuous.

13. The method of claim 10, wherein said disease or disorder is selected from the group consisting of Parkinson's disease or secondary parkinsonism.

14. The method of claim 13, wherein said disease is Parkinson's disease.

15. The method of claim 14, wherein said administering is continuous.

16. The method of claim 15, wherein said administering is intraduodenal.

17. An infusion pump comprising the composition of claim 1.

* * * * *